United States Patent [19]

Haynie

[11] Patent Number: 5,847,047

[45] Date of Patent: Dec. 8, 1998

[54] ANTIMICROBIAL COMPOSITION OF A POLYMER AND A PEPTIDE FORMING AMPHIPHILIC HELICES OF THE MAGAININ-TYPE

[75] Inventor: Sharon Loretta Haynie, Philadelphia, Pa.

[73] Assignee: E. I. du Pont de Nemours and Company, Wilmington, Del.

[21] Appl. No.: 569,188

[22] PCT Filed: Jun. 22, 1994

[86] PCT No.: PCT/US94/07019

§ 371 Date: Dec. 18, 1995

§ 102(e) Date: Dec. 18, 1995

[87] PCT Pub. No.: WO95/00547

PCT Pub. Date: Jan. 5, 1995

Related U.S. Application Data

[63] Continuation-in-part of Ser. No. 82,852, Jun. 22, 1993, abandoned.

[51] Int. Cl.⁶ .................................................. C08G 63/00
[52] U.S. Cl. ........................ 525/54.1; 530/326; 530/300
[58] Field of Search ................................... 530/326, 300; 525/54.1

[56] References Cited

U.S. PATENT DOCUMENTS

| | | | |
|---|---|---|---|
| 4,496,363 | 1/1985 | DeFilippi | 8/115.5 |
| 4,810,567 | 3/1989 | Calcaterra et al. | 428/224 |
| 5,008,371 | 4/1991 | Natori | 530/324 |
| 5,019,093 | 5/1991 | Kaplan et al. | 606/228 |
| 5,073,542 | 12/1991 | Zasloff | 514/12 |
| 5,096,886 | 3/1992 | Boman et al. | 514/12 |

FOREIGN PATENT DOCUMENTS

| | | |
|---|---|---|
| 0453621 | 10/1991 | European Pat. Off. |
| WO 89/04371 | 5/1989 | WIPO |
| WP 90/04408 | 5/1990 | WIPO |
| WO 90/06129 | 6/1990 | WIPO |
| WO 92/01462 | 2/1992 | WIPO |
| WO 92/17197 | 10/1992 | WIPO |
| WO 92/18146 | 10/1992 | WIPO |
| WO 92/22317 | 12/1992 | WIPO |
| WO 94/13697 | 6/1994 | WIPO |

OTHER PUBLICATIONS

Suenaga (1989) Biochim. Biophys. ACTA, 981, pp. 143–152.
Duran, (1993) Abstracts of the 19th Annual Meeting of the Soc. for Biomaterials, p. 35.
Abstract of WO 89/04371, Mar. 19, 1990.
Goldstein, (1981) J. Chromatog. 215, pp. 31–43.
Lin et al. (1992) J. Biomater. Sci. Polymer Ed. 3/3, pp. 217–227.
Lee et al. (1986) Biochim. Biophys. ACTA, 862, pp. 211–219.
DeGrado (1983) Peptides: Structure and Function, 195–198.
Zasloff (1987) Proc. Natl. Acad. Sci. USA, vol. 84, pp. 5449–5453.
Chen et al. (1988) FEB, vol. 236, pp. 462–466.
Peck–Miller et al. (1993) Cancer Chemother. Pharmacol., vol.32, pp. 109–115.
Jaynes et al. (1990) GenBank database, Accession No. P91350.
Jaynes et al. (1990) GenBank database, Accession No. P91335.

*Primary Examiner*—Robert A. Wax
*Assistant Examiner*—Enrique D. Longton

[57] ABSTRACT

Novel polymer-bound oligopeptides exhibiting antimicrobial activity have been develop. The oligopeptides are unique amino acid sequences that form amphiphilic helices.

6 Claims, 7 Drawing Sheets

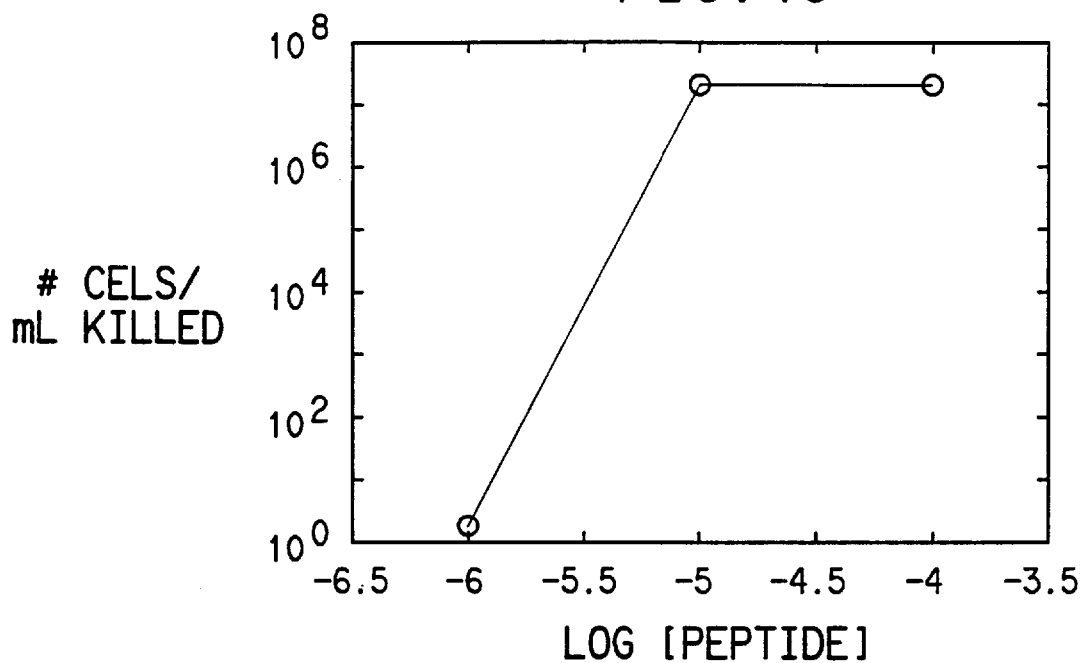
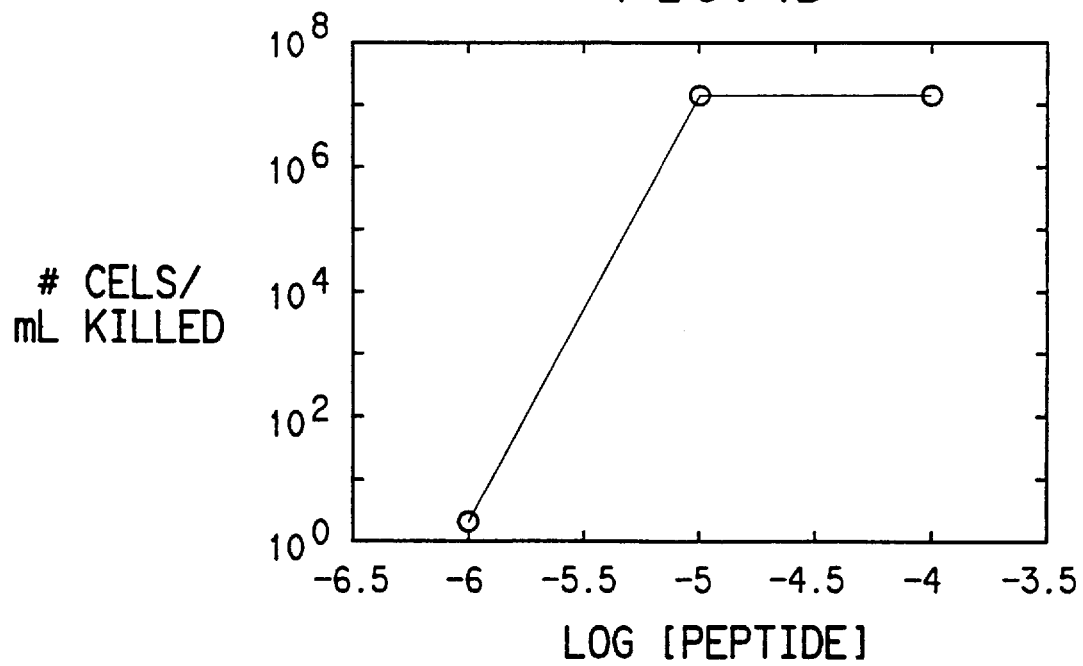

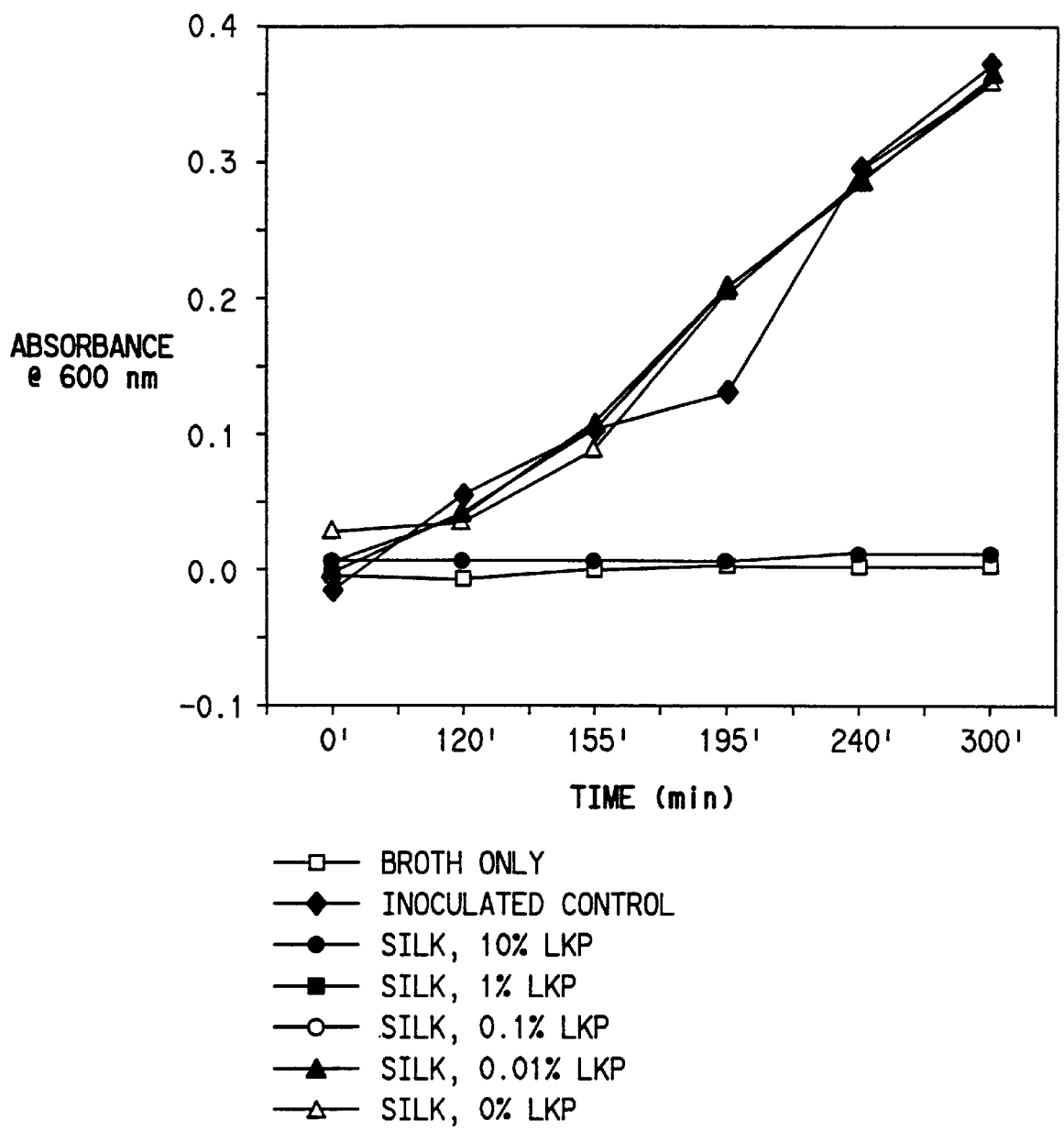

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Lys  Gly  Leu  Lys  Lys  Leu  Leu  Lys  Leu  Leu  Lys  Lys  Leu  Leu  Lys  Leu
 1              5                         1 0                        1 5
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
Leu  Lys  Leu  Leu  Lys  Lys  Leu  Leu  Lys  Leu  Leu  Lys  Lys  Leu  Gly  Lys
 1              5                         1 0                        1 5
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Lys  Gly  Gly  Leu  Lys  Lys  Leu  Leu  Lys  Leu  Leu  Lys  Lys  Leu  Leu  Lys
 1              5                         1 0                        1 5
Leu
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Leu Lys Leu Leu Lys Lys Leu Leu Lys Leu Leu Lys Lys Leu Gly Gly
1               5                   10                  15
Lys
```

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
Lys Gly Gly Gly Leu Lys Lys Leu Leu Lys Leu Leu Lys Lys Leu Leu
1               5                   10                  15
Lys Leu
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

```
Leu Lys Leu Leu Lys Lys Leu Leu Lys Leu Leu Lys Lys Leu Gly Gly
1               5                   10                  15
Gly Lys
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
Leu Lys Lys Leu Leu Lys Lys Leu Lys Lys Leu Lys Lys Leu Leu Lys
1               5                   10                  15
Leu
```

( 2 ) INFORMATION FOR SEQ ID NO:8:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:8:

```
Leu Lys Lys Leu Leu Lys Leu Leu Lys Lys Leu Leu Lys Leu
1               5                   10
```

-continued ( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:9:

```
Leu  Lys  Lys  Leu  Leu  Lys  Leu
1                 5
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:10:

```
Lys  Gly  Leu  Lys  Lys  Leu  Leu  Lys  Leu  Leu  Lys  Lys  Leu  Leu  Lys  Leu
1                 5                          10                         15
```

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Lys  Gly  Leu  Lys  Lys  Leu  Leu  Lys  Leu  Leu  Lys  Lys  Leu  Leu  Lys  Leu
1                 5                          10                         15
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Lys  Gly  Leu  Lys  Lys  Leu  Leu  Lys  Leu  Leu  Lys  Lys  Leu  Leu  Lys  Leu
1                 5                          10                         15
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Leu  Lys  Leu  Leu  Lys  Lys  Leu  Leu  Lys  Leu  Leu  Lys  Lys  Leu  Gly  Lys
1                 5                          10                         15
```

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:14:

```
Leu Lys Leu Leu Lys Lys Leu Leu Lys Leu Leu Lys Lys Leu Gly Gly
1               5                   10                  15
Lys
```

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:15:

```
Leu Lys Leu Leu Lys Lys Leu Leu Lys Leu Leu Lys Lys Leu Gly Gly
1               5                   10                  15
Gly Lys
```

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:16:

```
Ser Asn Met Ile Glu Gly Val Phe Ala Lys Gly Phe Lys Lys Ala Ser
1               5                   10                  15
His Leu Phe Lys Gly Ile Gly
                20
```

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:17:

```
Val Phe Ala Lys Gly Phe Lys Lys Ala Ser His Leu Phe Lys Gly Ile
1               5                   10                  15
Gly
```

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown ( i i ) MOLECULE TYPE: peptide ( x i ) SEQUENCE DESCRIPTION: SEQ ID NO:18:

Gly Ile Gly Lys Phe Leu His Ser Ala Lys Lys Phe Gly Lys Ala Phe
1               5                   1 0                 1 5

Val Gly Glu Ile Met Asn Ser
            2 0

ANTIMICROBIAL COMPOSITION OF A POLYMER AND A PEPTIDE FORMING AMPHIPHILIC HELICES OF THE MAGAININ-TYPE

CROSS-REFERENCE

This case is the National Stage of International Application No. PCT/US94/07019, filed Jun. 22, 1994, under 35 USC 371, a Continuation-In-Part of U.S. application Ser. No. 08/082,852, filed Jun. 22, 1993, now abandoned, benefit of which is claimed.

FIELD OF INVENTION

The invention relates to the design and synthesis of novel antimicrobial compositions comprising unique amino acid sequences that form amphiphilic helices and possess antimicrobial properties. More specifically, the invention provides the peptides of amino acid sequences KGLKKLLKLLKKLLKL,(SEQ ID NO:1) LKLLKKLLKL LKKLGK(SEQ ID NO:2) KGGLKKLLKLLKKLLKL (SEQ ID NO:3), LKLLKKLLKLLKKLGGK (SEQ ID NO:4) and KGGGLKKLLKLLKKLLKL (SEQ ID NO:5) LKLLKKLLKLLKKLGGGK (SEQ ID NO:6) where these peptides have the capability of killing microorganisms without being indiscriminately cytotoxic. The invention further relates to the incorporation of these and other antimicrobial peptides into polymer compositions without limiting the bioactivity of the peptides.

BACKGROUND OF THE INVENTION

Many vertebrates and invertebrates secrete natural substances that possess both antibacterial and/or indiscriminate cytotoxic properties. Examples of some of these substances include PGLa (frog skin), defensins (human phagocytes), cecropins (Silkmoth pupae or pig intestine), apidaecins (honeybee lymph), melittin (bee venom), bombinin (toad skin) and the magainins (frog skin). Purification of the active constituents of these natural substances have shown that they consist primarily of protein and it has been suggested that they may constitute a system of cellular immunity in the producing organism.

Peptides and oligopeptides that have activity against microorganisms span a broad range of molecular weights, secondary conformations and sites of action. Biological activity can range from being specifically bactericidal or fungicidal to being indiscriminately cytotoxic (cell lytic) to all cells. Peptides that are specifically bactericidal include large polypeptides such as lysozyme (MW 15000 daltons) and attacins (MW 20–23,000 daltons) as well as smaller polypeptides such as cecropin (MW 4000 daltons) and the magainins (MW 2500 daltons). The spectrum of biocidal activity of these peptides is somewhat correlated to size. In general, the large polypeptides are active against limited types and species of microorganisms (e.g., lysozyme against only gram positive bacteria), whereas many of the smaller oligopeptides demonstrate a broad spectrum of antimicrobial activity, killing many species of both gram positive and gram negative bacteria.

Although few similarities exist between the amino acid sequences of the biocidal peptides, it has been shown that magainin, cecropins, and bombinin oligopeptides form similar secondary structures described as an amphiphilic helix (Kaiser et al. *Annu. Rev. Biophys. Biophys. Chem* 16, 561–581, 1987). Amphiphilic or amphipathic helices are secondary protein structures possessing an overall affinity for hydrophillic materials. It has been suggested that the affinity of these helices for cell membranes may account, in part, for their biological activity and the literature would suggest that there may be a strong correlation between this secondary peptide structure and biological activity (Lee et al. *Biochem. Biophys. Acta* 862, 211–219, (1986)).

One of the first biocidal oligopeptides to be isolated from natural sources was bombinin and is described by Csordas et al. (*Proc. Int. Symp. Anim. Plant Toxins,* 2, 515–523, (1970) ). Bombinin is found in toad skin secretions and has both antimicrobial and cytotoxic properties. Csordas teaches significant sequence homology between bombinin and melittin, another antimicrobial peptide, isolated from bee venom.

DeGrado and Kezdy (*J.A.C.S.* 103, 679–681,(1981)) describe the preparation of potent synthetic analogues of melittin using rational peptide design. The peptide sequences of DeGrado were shown to have both structural and functional similarities to melittin in that both attained similar amphiphillic helical secondary conformation and both were indiscriminately cytotoxic. Subsequently DeGrado et al. (*Peptides: Structure and Function., Proc.* 8th *Amer. Peptide Symp.,* V. J. Hruby Ed., (1983)) prepared a series of idealized synthetic oligopeptides to mimic the cecropins. These cecropins analogues were Fmoc blocked peptides containing Leu and Lys repeats and mimicked the bioactivity of their natural counterparts.

Zasloff et al. (WO 9004408) describe the use of the amphiphilic forming peptide, magainin and magainin fluoride analogues as pharmaceutical compositions. The peptides of Zasloff are limited in size to between 16 and 50 amino acids, and consist of blocks of four amino acids, each block containing at least one hydrophobic, one hydrophillic neutral, and one hydrophillic basic amino acid.

Cuervo et al. (WO 9006129) describe the preparation of deletion analogues of magainin I and II for use as pharmaceutical compositions. They disclose a general scheme for the synthetic preparation of compounds with magainin-like activity and structure.

From the art it would appear that biological activity of these peptides is not only dependent on secondary structure but also is related to sequence length. For most peptides there exists an amino acid minimum below which antimicrobial activity is reduced or eliminated. The sequences of Cuervo (WO 9006129), for example, contain a minimum of nine unique amino acids for antimicrobial activity. Bomen et al. in U.S. Pat. No. 5,096,886 describe a natural cecropin isolated from pig intestine that contains a minimum of twelve unique amino acids. A minimum of thirteen unique amino acids are present in the sequence for the antimicrobial polypeptide secreted from Sarcophaga peregrina embryo as described by Natori in U.S. Pat. No. 5,008,371.

Although the antimicrobial and cytotoxic activities of the above mentioned preparations are good, they all consist of proteins that must be isolated and purified from natural sources. The isolation of large quantities of these peptides necessary for pharmaceutical and related uses is both impractical and expensive. Furthermore, many of the synthetic analogues described above contain a diversity of amino acids and the synthesis of such molecules is not trivial. Even though blocking strategies are improving in the art of peptide synthesis, the incorporation of certain amino acids (i.e., Histidine) still poses some difficulty in solid phase peptide synthesis (Stewart et al. *Solid Phase Peptide Synthesis,* 2nd Edit, J. M. Stewart, J. D. Young, 1984, Pierce Chem. Co. pp 18–27). Histidine is one of the unique amino acids in the core sequence described by Cuervo and Houghten (WO 9006129).

Lee et al. *Biochem. Biophys. Acta* 862, 211–219, (1986) describe the preparation of basic model synthetic peptides containing highly conserved amino acid sequences possessing antimicrobial activity specifically against gram positive bacteria. The peptides of Lee contain mixtures of Leu, Ala, Lys and Arg. The antimicrobial activities of these peptides roughly parallel their alpha helix content. Bioactivity of these peptides may be further correlated with the position of the basic and hydrophobic groups in the sequence. Thus high alpha-helix content corresponds to high biological activity and peptides where the hydrophobic groups and the hydrophilic cationic groups are segregated on the face of the helix, exhibit the most potent biological activity. Lee further teaches that the primary requirement for biological activity is the structure-forming potential of the sequence in a hydrophobic environment.

Although the peptides of Lee appear to be selectively active against gram positive bacteria as opposed to gram negative bacteria, Lee also teaches that synthetic sequences with Arg or Lys between short patches of hydrophilic amino acids cause leaking from mitochondrion, microsomes, lysosomes and red blood cells suggesting that these peptides do not highly discriminate among structures containing lipid bilayer membrane surfaces.

Suenaga et al. (*Biochem. Biophys. Acta* 981, 143–150, (1989)) teach that blocks of four, 4-mer peptides of the same or similar composition to those of Lee are capable of forming amphipathic helices and are useful in inducing the fusion of unilamellar lipid vesicles. These peptides were seen to cause extensive perturbation of the lipid bilayer prior to fusion, again emphasizing the interaction of these peptides with lipid bilayer structures.

Houghten et al. (WO 9201462) advanced the earlier work of Lee and Suenaga teaching oligopeptides which have activity against both gram positive and gram negative bacteria without being indiscriminately cytotoxic. The model oligopeptide of Houghten consists of a sequence that contains only Lys and Leu amino acids of the formula SEQ ID NO:7. Houghten teaches that there is no antimicrobial activity when the length of the peptide exceeds 25 amino acids or contains less than 8 amino acids and that she most active sequences contain hydrophilic content of between 50 and 60%. Furthermore, when the charge content of the sequence exceeds 54% the oligopeptide loses potent activity against gram negative bacteria even though an amphiphillic secondary structure is maintained.

Buttner et al. (*Biopolymers* 32, 547–583, (1992)) describe the relationship between antimicrobial activity and alpha helix content of a peptide. Buttner teaches that preservation of the hydrophobic side of the helix is important to the potency of the antimicrobial activity. Thus, it would appear that antimicrobial peptides as taught by Lee or Houghten must additionally have a proper balance of hydrophobic and hydrophilic amino acids and these amino acids must be judiciously placed in the sequence such that an alpha helix secondary structure can be achieved in the presence of a hydrophobic environment.

The peptides described above are useful, however, each have significant drawbacks. The peptides of Lee, although synthetic and containing a simpler composition than those isolated from nature, still contain a significant percentage of Ala and Arg which contribute to the complexity of the synthesis of the sequence. Although the simpler peptides of Houghten contain only Leu and Lys they require a relatively high percentage of the basically charged amino acid Lys. The requirement for a high percentage of Lys limits these sequences in light of the further necessity of having peptides with a basic charge content of less than 54% to maintain biological activity.

WO-A-92/2317 discloses amino acid compositions comprising a C-terminal substituted peptide of the formula X-CO-T where X is an amphiphilic peptide and T comprises a variety of substituents.

There remains a need, therefore, for an antimicrobial peptide of simple composition, active against both gram negative and gram positive bacteria that contains a low percentage of basic charged amino acids that lends itself to production in commercial quantities.

The composition of the present invention represents an improvement over the prior art, providing a sequence that is simple and adaptable for commercialization, that demonstrates activity against both gram positive and negative bacteria without being indiscriminately cytotoxic, and that has a lower Lys (or basic, charged amino acid) content than the sequences taught in the art. The lower Lys content of the sequences of the instant invention render them more versatile, permitting substitution of other hydrophilic amino acids for Lys without decreasing bioactivity.

The expanding needs in the medical and fabrics industries for maintaining sterile and odor free environments has led to the development of materials with inherent antimicrobial properties. For the most part, polymers and polymer compositions have been targeted for enhancement with antimicrobial agents. Methods of rendering polymers antimicrobial are varied, and include the incorporation of metals and metal ions into the polymer, the use of various polymer coatings such as alpha or beta chitins and metal containing zeolites, or irradiation of polymer fibers to produce surface active antimicrobial groups such as quaternary or tertiary amines (White et al., *Chemically Modified Surfaces*, Vol. 1 *Silanes, Surfaces & Interfaces*, D. E. Leyden, Edit. 1985, 107–140. and Goldstein, L, *Journal of Chromatoaraphy*, 215, 31, (1981)). The above methods all rely on reactive groups on the surface of the polymer to provide the antimicrobial function.

Alternatively, antimicrobial polymers have been designed where the antimicrobial moiety is released from the polymer surface. Shiraishi et al. (*J. Macromol Sci-Chem* A25 (8) 1015–1025, (1988)) describe the preparation of polymer derivatives of chloramphenicol which acts as an inhibitor of protein synthesis. Chloramphenicol release from the polymeric precursor prodrug is required for activity against microorganisms. Dumitriu et al. (*Coll & Poly. Sci.* 267:595–599 (1989)) describe bioactive polymers with coupled chloramphenical and ampicillin. Singh et al. (*Die Angew. Makromol. Chemie,* 172 87–102, (1989)) describe a method for radiation grafting of methacrylic acid onto silk to immobilized 8-hydroxyquinoline HCl. The drug is immobilized solely by electrostatic interaction and the antimicrobial activity is a result of sustained release of the drug into the media.

Formulas with unusual peptides and amino acids have been used in controlling the infection or growth of fungi on a variety of articles. For example, Schmatz et al. (GB 2241955) describe a cyclic hexapeptide containing hydroxy groups. Sato et al. (GB 2099301) describe the coating of synthetic fibers with solutions containing an amino acid surfactant containing a C8 to C16 fatty acid. The surfactant is comprised of non-natural amino acids and has a relatively low antimicrobial specific activity. Additionally the fatty acid constituents have a negative impact on the water solubility of the polymer compound. Bunyan (BE 844904)

describes the preparation of surgical dressing consisting of a film-forming protein and its treatment with hypochlorite to create a bactericidal. It is the Hypochlorite and not the polypeptide that is the disinfecting agent in the compositions of Bunyan. Unitika (JP 02091275) teaches the coating of a formed yarn with an antibacterial polyamino acid. Besides being antimicrobial the incorporation of the polyamino acid imparts a coating with a "softer touch" quality to the polymer.

The above mentioned amino acid containing antimicrobial polymers are useful, but are limited in that the bioactive component must be released from the fiber to effect antimicrobial activity. The leaching of bioactive moieties poses the potential problem of contaminating other materials with unwanted antimicrobial agents as well as limiting the effective life of the treated polymer. A preferred polymer composition would comprise an antimicrobial peptide chemical bonded to the polymer. Such a composition would represent an improvement over the art as it would overcome the problem of leaching of bioactive agents while at the same time possesing extended bioactive utility.

Kaplan et al. (U.S. Pat. No. 5,019,093) discloses a braided suture comprised of bioabsorbable polymeric materials which exhibits enhanced flexibility and hand. The suture may be mixed with a variety of antimicrobial aqents including magainin to convey antimicrobial properties to the suture.

Calcaterra et al. (U.S. Pat. No. 4,810,567) describe the preparation of antimicrobial fabrics by irradiation of a vinyl-modified polymyxin onto fabrics of a variety of chemical composition. The resultant antimicrobial polymer is active due to the covalent bonding of polymyxin to the fabric. A hydrolyzable material would be detrimental to this invention. This particular cyclic peptide antibiotic is not selective and according to Franklin and Snow (Biochemistry of Antimicrobial Action, 4th Edition, Chapman & Hall, London 1989, pp. 61–62) the polymyxins have minor medicinal value because they also target mammalian membranes. In addition, the process of Calcaterra et al. is fairly non-selective and does not ensure that the cyclic peptide will be attached to the surface in a manner that optimally presents the antibiotic to the outer membrane. Finally, polymyxins are not very active against gram positive bacteria. The classes of antimicrobials described in U.S. Pat. No. 4,810,567 do not include the antimicrobial peptides described herein.

Recent advances in peptide synthesis and recombinant genetics have made it both feasible and practical to use natural and synthetic peptides as bioactive agents in polymer compositions. Polymers with covalently bonded peptides or polypeptides are known. For example, RGD-containing sequences have been covalently incorporated into polyurethanes (Lin et al., *J. Biomater. Sci. Polym. Ed.* 3, 217–227, (1992)) for the purpose of providing biomaterials for therapeutic use. The RDG peptide sequences may be incorporated either as side chains or directly into the polymer backbone and still retain bioactivity. The principle function of the RDG and other peptide sequences to facilitate is the selective adhesion and growth of mammalian cells such as endothelial cells on the surface of the polymer. Additionally there are numerous examples of the covalent binding of larger polypeptides, proteins and enzymes to polymers which function as immobilized biocatalysts.

Recently Duran, L. W., et al., (*Soc. Biomater.*, 19th Annual Meeting, April–May Vol. 26, p. 35 (1993)) have disclosed the covalent photochemical immobilization of magainin on silicon rubber. It was demonstrated that the photoderivatized magainin was active against both gram positive and gram negative bacteria and that the silicon rubber-peptide composition was active against *S. epidermidis*. The teaching of Duran et al., show that, in one instance, bioactive magainin may be covalently linked to a rubber polymer, however, do not teach the method of that attachment nor the covalently linking of any other antimicrobial peptides to polymers. Furthermore, Duran et al., teach compositions with very low bioactivities making it unlikely that such compositions would be practical in commercial applications.

The present invention provides a polymer composition comprising a bioactive covalently bonded antimicrobial peptide. The covalent bonded antimicrobial peptide polymer is regenerable after use and thus has considerably extended lifetime over the such systems whose mechanism of action relies on the leaching or hydrolysis of the bioactive peptide into the soluble fluids.

SUMMARY OF THE INVENTION

The present invention provides a series of non-natural oligopeptides useful as antimicrobial agents. These oligopeptides are related in that they share a common amino acid sequence, referred to as the core oligopeptide. The core oligopeptide has antimicrobial activity against gram negative and gram positive bacteria and against yeasts. More particularly, this invention provides analogues of the core oligopeptide, wherein at least one amino acid residue has been added to either the amino terminus or the carboxy terminus of the core oligopeptide chain, where additions to the amino terminus are prefered. The preferred analogues are referred to as N-addition analogues and their sequences are given, along with the core oligopeptide in Table I. The N-addition analogues have greater antimicrobial activity than the core oligopeptide. The oligopeptides of the present invention have an amphiphilic helical secondary structure resembling naturally occurring antimicrobial peptides and the shape is considered essential to antimicrobial activity.

TABLE I

Sequences of Non-Natural Oligopeptides with Antimicrobial Activity

| Formula # | -4 | -3 | -2 | -1 | 1 | 2 | 3 | 4 | 5 | 6 | 7 | 8 | 9 | 10 | 11 | 12 | 13 | 14 | |
|---|---|---|---|---|---|---|---|---|---|---|---|---|---|---|---|---|---|---|---|
| I | | | | | Leu | Lys | Lys | Leu | Leu | Lys | Leu | Leu | Lys | Lys | Leu | Leu | Lys | Leu | (SEQ ID NO:8) |
| II | | | Lys | Gly | Leu | Lys | Lys | Leu | Leu | Lys | Leu | Leu | Lys | Lys | Leu | Leu | Lys | Leu | (SEQ ID NO:1) |

TABLE I-continued

Sequences of Non-Natural Oligopeptides with Antimicrobial Activity

| Formula # | -4 | -3 | -2 | -1 | 1 | 2 | 3 | 4 | 5 | 6 | 7 | 8 | 9 | 10 | 11 | 12 | 13 | 14 | |
|---|---|---|---|---|---|---|---|---|---|---|---|---|---|---|---|---|---|---|---|
| III | | Lys | Gly | Gly | Leu | Lys | Lys | Leu | Leu | Lys | Leu | Leu | Lys | Lys | Leu | Leu | Lys | Leu | (SEQ ID NO:3) |
| IV | Lys | Gly | Gly | Gly | Leu | Lys | Lsy | Leu | Leu | Lys | Leu | Leu | Lys | Lys | Leu | Leu | Lys | Leu | (SEQ ID NO:5) |

The present invention further provides a biologically active amphiphilic oligopeptide, said oligopeptide being of the general formula V: Formula V:

(R—Cx)y-(ABBAABA)z, wherein:

x=0, 1, 2, or 3;

y=0,1;

z=>1;

R=X—(CH2)n—CH(Y)—C(O) where n=1–6;

X=—NH2, NH2—C(O)—NH—C(NH2)=NH, or —C(NH2)=NH;

Y=X, H or —NH(Bl) where Bl is a common blocking group such as acetyl;

A=Leu, Met, Phe, Ala, Val or Ile;

B=Lys, Arg, His, Gln, Asn, Ser, Thr and Orn (Ornithine); and

C=Gly or Ala.

The instant invention further provides a polymer-oligopeptide composition comprising of a polymer, and an oligopeptide of formula V wherein the polymer is selected from the group consisting of polyurethane, polyetherurethane, polyester, silicone, polyamide, polyolefin, polypeptide, polysaccharide, cellulosic, or silk. The polymer-oligopeptide compositions may comprise the oligopeptide coated on the surface of the polymer or covalently incorporated in the polymer as side chain moieties. The oligopeptide is not consumed by the microbial cell and therefore may act many times. Consequently less peptide is necessary as part of the composition and there is less chance that mircoorganisms will develop resistance to these oligopeptides.

Also provided is a process for inhibiting the growth of microorganism comprising the steps of: contacting an effective amount of a polymer-oligopeptide composition with a population of microorganisms; and leaving the polymer-oligopeptide in contact with the microorganism population for a time sufficient to inhibit microorganism growth.

Additionally a process is provided for the production of an antimicrobial oligopeptide-polymer composition comprising the steps of: modifying a suitable polymer by the addition of a non-clevable linker group; synthesizing an Fmoc blocked peptide using Fmoc blocked amino acids and the techniques of solid phase peptide synthesis wherein the first amino acid of the peptide to be synthesized is joined to the non-clevable linker; and deprotecting the Fmoc blocked peptide.

BRIEF DESCRIPTION OF THE DRAWINGS AND SEQUENCE LISTINGS

FIG. 1 illustrates a general scheme for stepwise solid phase peptide synthesis, where R=insoluble polymeric support; AA1, AA2 . . . AAn=amino acid residues numbered starting from C-terminus; T="temporary" protection; O="permanent" protection over the course of peptide synthesis; ⊣=free carboxyl; ⊢=free amino FIG. 2 illustrates reactions for synthesis of monoamine and bisamine oligopeptides derivatives.

FIG. 4c illustrates cell growth inhibition of E. coli by the N-addition analogue corresponding to formula III.

FIG. 4d illustrates cell growth inhibition of E. coli by the N-addition analogue corresponding to formula IV.

FIG. 5 illustrates cell growth inhibition of E. coli by a silk-core oligopeptide composition.

Figure 1:
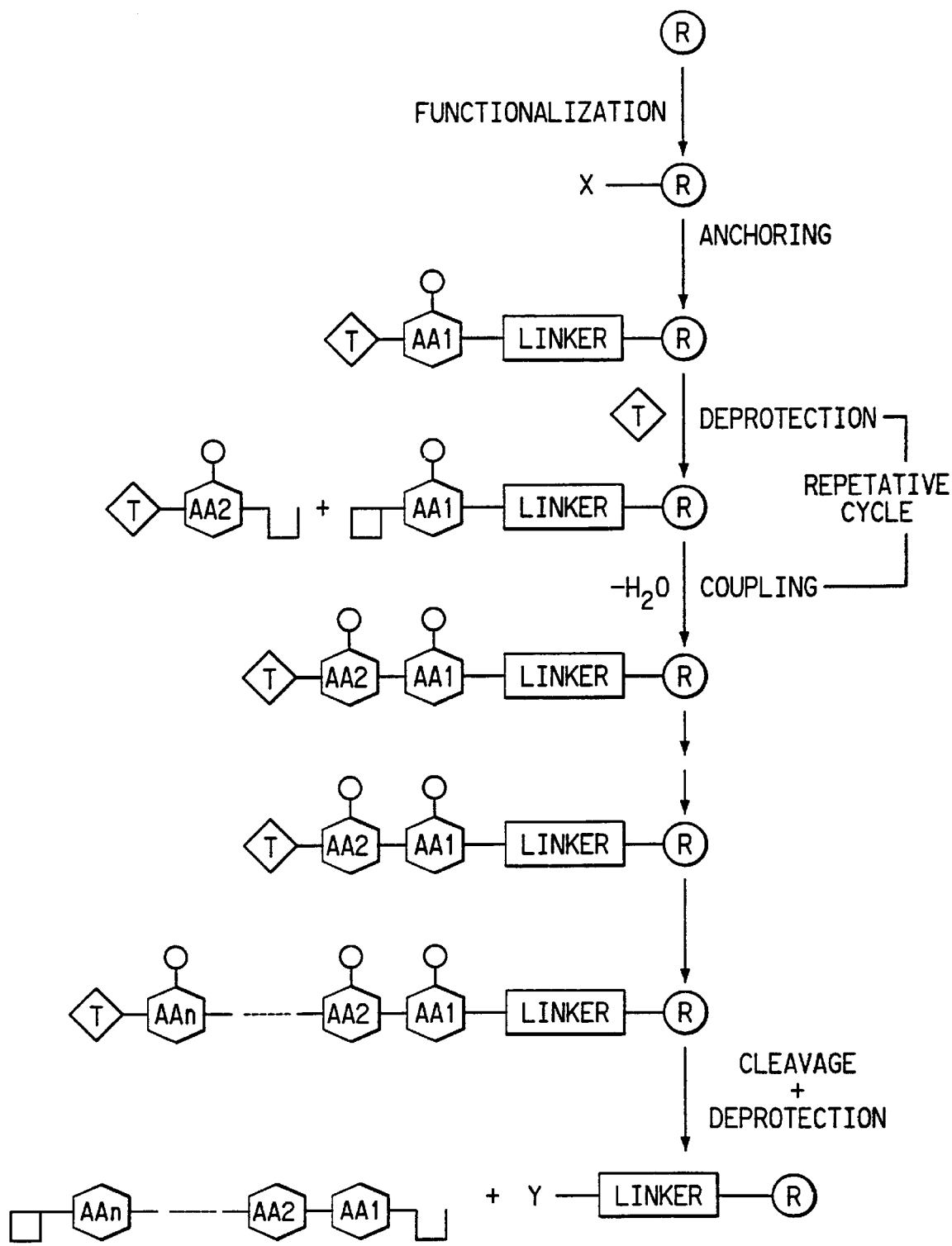

Applicant provides Sequence Listings 1–18 in conformity with "Rules for the Standard Representation of Nucleotide and Amino Acid Sequences in Patent Applications" (Annexes I and II to the Decision of the President of the EPO, published Supplement No. 2 to OJ EPO 12/1992).

DETAILED DESCRIPTION OF THE INVENTION

As used herein the following terms may be used for interpretation of the claims and specification.

The terms "peptide" and "oligopeptides" will be used interchangably and will refer to amino acid sequences of between two and thirty amino acids in length.

The term "core oligopeptide" will refer to peptides given by the formula (Leu-Lys-Lys-Leu-Leu-Lys-Leu)$_n$ (SEQ ID NO:9) wherein the amino acid sequence occurs from left to right as shown or from right to left and where n=1, 2, or 3. The core oligopeptide will also be indicated by the abbreviation "LKP".

The term "antimicrobial" means as having to do with the killing or growth inhibition of microbial organisms.

The term "cytotoxic" means the killing or lysis of eukaryotic organisms.

Ther terms "amphiphillic helix" and "amphipathic helix" are used interchangably and mean any protein or peptide secondary structure that forms a helix wherein that helix includes both hydrophobic and hydrophilic regions and demonstrates an affinity for hydrophillic structures such as those found in lipid bilayers and cell membranes.

The term "class A amino acids" refers to those amino acids with a net hydrophobic affinity.

The term "class B amino acids" refers to those amino acids with a net negative electrostatic charge.

The term "class C amino acids" refers to amino acids selected from the group consisting of Gly or Ala.

The term "N-addition analogue" refers to any derivative of the core oligopeptide amino acid sequence where at least one amino acid is added to either the N-terminal or the carboxy end of the core oligopeptide where additions to the amino terminus are preferred. The amino acid additions to the core oligopeptide may be of any type being either natural or non-natural, hydrophobic, hydrophilic or basic. The preferred N-addition analogues of the instant invention will be abbreviated SEQ ID NO:1, SEQ ID NO:3, and SEQ ID NO:5 corresponding to the formulae II, III, and IV of Table I respectively.

The terms "side chain blocking group" or "side chain protecting group" refers to labile chemical groups that are covalently attached to a chemically-reactive site on the amino acid. The blocking or protecting group acts to prevent chemically-reactive sites from competing or interfering with the desired specific coupling of an alpha amino group of one amino acid to a carboxyl group on another amino acid to form a peptide bond. The blocking or protecting group is labile to allow selective removal under appropriate conditions. Common blocking groups may include, but are not limited to acetyl (Ac), trifluoroacetyl (Tfa), tert-butyloxycarbonyl (Boc), benzoyl (Bz), and 9-fluorenylmethyloxycarbonyl (Fmoc).

The term "non-cleavable linker" refers to any chemical moiety or compound capable of modifying a suitable polymer through which a covalent attachment of an oligopeptide may be accomplished. A typical example of a non-cleavable linker is ethylenediamine (EDA).

The term "MIC" refers to minimal inhibitory concentration and will be defined as the lowest concentration of either soluble peptide or peptide immobilized on a polymer that results in total kill of bacteria.

The term "DIC" refers to the compound diisopropyl carbodiimide.

The term "DMAP" refers to the compound dimethylaminopyridine.

The term "NMM" refers to the compound N-methylmorpholine.

The term "DCM" refers to the compound dichloromethane.

The term "DMF" refers to the compound dimethylformamide.

The term "DIEA" refers to the compound N,N'-diisopropylethylamine.

The term "Castro's reagent" and "BOP" are used interchangeably and are defined as the mixture of compounds comprising (benzotriazole-1-yl-oxy-tris (dimethylamino) phosphoniumhexafluorophosphate).

As used herein the following abbreviations will be used to identify specific amino acids:

| Amino Acid | Three-Letter Abbreviation | One-Letter Symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Peptides of the present invention are effective as antibiotics and can be employed to inhibit, prevent or destroy the growth or proliferations of microorganisms such as Gram-positive and Gram-negative bacteria, fungi and yeasts.

The peptides can also be used as preservative or sterilants for material susceptible to microbial contamination.

The peptides of the present invention can be administered to a target cell or host by direct or indirect application. For example, the peptide may be administered topically or systemically.

The peptides of the present invention may be incorporated into films or spinnable fibers for their use in sterilants of material susceptible to microbial contamination.

The covalently bonded peptide-polymer compostions of the instant invention may be used as therapeutics or prophylactics on surfaces where microbial contamination is a problem such as delivery vehicles for foods, seeds, wound dressings, sutures, catheters, dialysis membranes, water filters, carpets and surgical gowns. Additionally the properties of this compostion are useful for both short term and long-term dwelling articles such as in fabrics, carpets, and catheters. Peptide design:

The present invention provides a series of non-natural oligopeptides useful as antimicrobial agents having in common the core oligopeptide. The core oligopeptide may be given by the formula:

(Leu-Lys-Lys-Leu-Leu-Lys-Leu)$_n$  (SEQ ID NO:9)

wherein the amino acid sequence occurs from left to right as shown or from right to left and where n =1, 2, or 3. Core oligopeptides have antimicrobial activity against gram negative and gram positive bacteria and against yeasts but are not indiscriminately cytotoxic. It is preferred that the core oligopeptide be composed of amino acids with either an all D- or all L-configuration. The directionality of the handedness of the resulting helical D and L peptides are opposing, however, the antimicrobial activity of the peptides are identical to each other. It is also contemplated that introduction of a small number of D-amino acids into the right-handed alpha helical peptides or a small number of L-amino acids into the predominantly D-amino acid, left-handed helices would be possible without significantly altering the biological activity of the composition.

The length of the core oligopeptide is variable in this invention. The core oligopeptide may be as short as seven amino acids and as long as twenty-one, where a length of at least fourteen amino acids is preferred.

The core oligopeptide comprises both hydrophobic (hereinafter referred to as class A amino acids) and basic amino acids (hereinafter referred to as class B amino acids) where an excess of hydrophobic amino acids is preferred and where a ratio of hydrophobic to basic amino acids of about 4:3 is most preferred. In a preferred embodiment the core oligopeptide contains at least fourteen amino acids where eight of the amino acids are hydrophobic and six amino acids are basic amino acids.

It will be appreciated by one of skill in the art that variants of the core oligopeptide are possible where suitable hydrophobic, hydrophillic and basic amino acids may be substituted for those of the present sequence with negligible affect on the bioactivity of the peptide. For the purpose of the such substitutions suitable class A amino acids may be selected from the group comprising Leu, Met, Phe, Ala, Val and Ile where Leu is most preferred. Suitable class B amino acids may be selected from the group comprising Lys, Arg, His, Gln, Asn, Ser, Thr and Orn (Ornithine), where Lys is most preferred.

The oligopeptide chain of the core oligopeptide is composed of blocks of three and occasionally two amino acids. Each block consists of at least one class A and one class B amino acid where the third amino acid in the group may be of class A or class B and where it is preferred that the third amino acid lie adjacent to the amino acid of its class (e.g., AAB or BAA or ABB or BBA). In designing variants of the core oligopeptide the groups of three amino acids should be placed next to each other in the oligopeptide such that the class A amino acids are in pairs and each pair of class A amino acids is spaced by at least one class B amino acid, but preferably two B amino acids (e.g., ABBAABAAB-BAABA; AABBAABABBAABA).

The invention further provides sequences derived from the core oligopeptide (hereinafter referred to as N-addition analogues) where the core oligopeptide is extended at either the amino terminus or the carboxy terminus with at least two and up to four amino acids. For the purposes of the present invention N-addition analogues comprising the addition of amino acids at the N-terminus of the core oligopeptide are preferred.

The N-terminal amino acid of the N-addition analogue may be any natural or non-natural amino acid that has the formula R=X—(CH2)n—CH(Y)—C(O) where n=1–6; X=—NH2, NH2—C(O)—NH—C(NH2)=NH, or —C(NH2)=NH; and Y=X, H or —NH(Bl) where Bl is a common blocking group. However, for the purposes of the present invention the N-terminal amino acid most preferred is Lys. The amino acids which intervene between the N-terminal Lys and the core oligopeptide will be referred to as class C amino acids and are selected from the group comprising Gly or Ala. The general sequence formula corresponding to these antimicrobial N-addition analogues is (R—Cx)y-(ABBAABA)z where x =0, 1, 2, or 3 and y=0,1 and z=>1. The N-addition analogues described by formulae II, III, and IV (Table I) are most preferred. As with the core oligopeptide the sequences of these N-addition analogues may be composed of all D- or all L-amino acids and the antimicrobial activity of the resulting all D- or all L-oligopeptides will be the identical to each other.

Figure 3A:
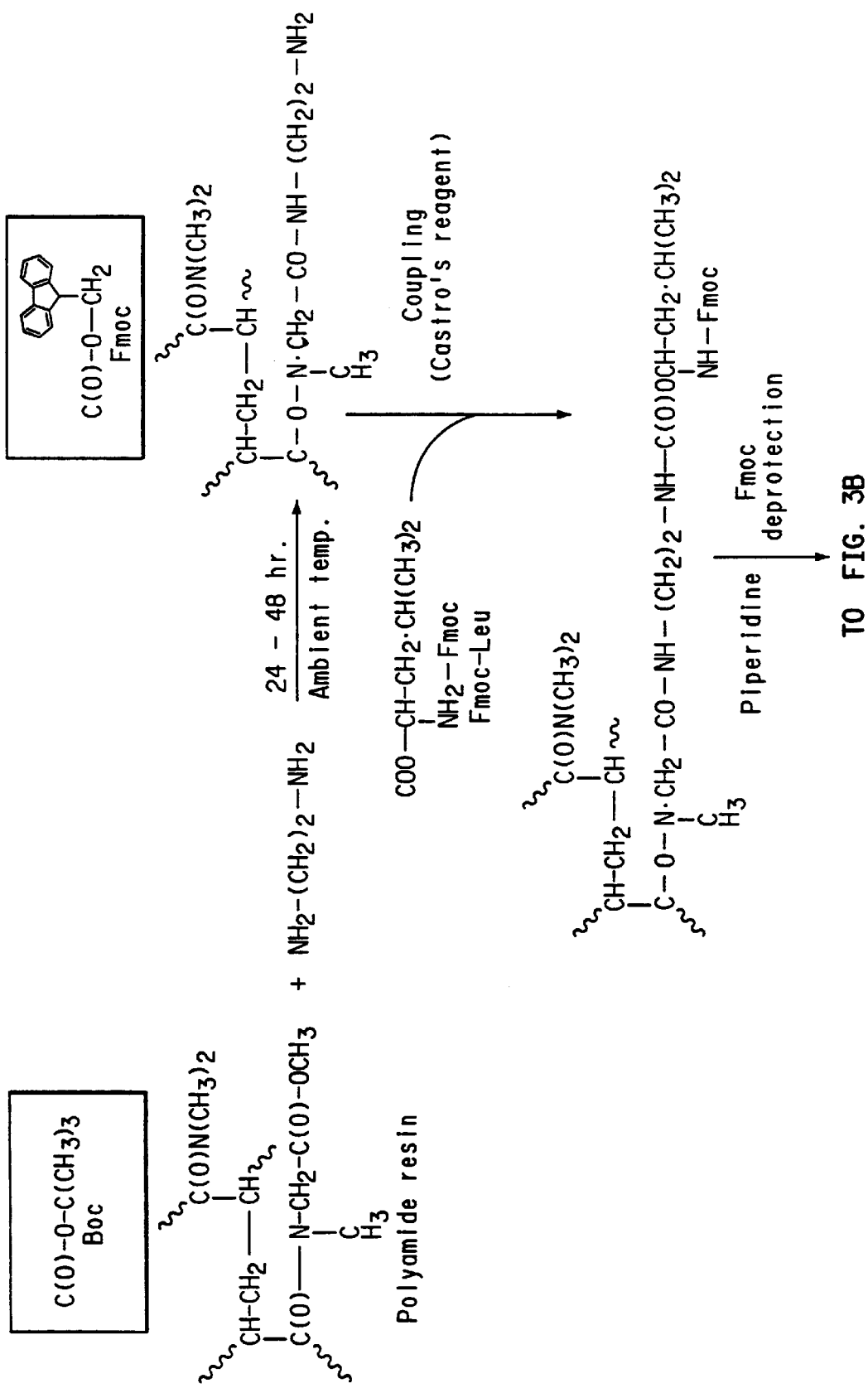
FIG. 3a and 3b illustrate a general reaction method for the covalent attachment of oligopeptides corresponding to formulas I–IV into a polyamine polymer.
Figure 3B:
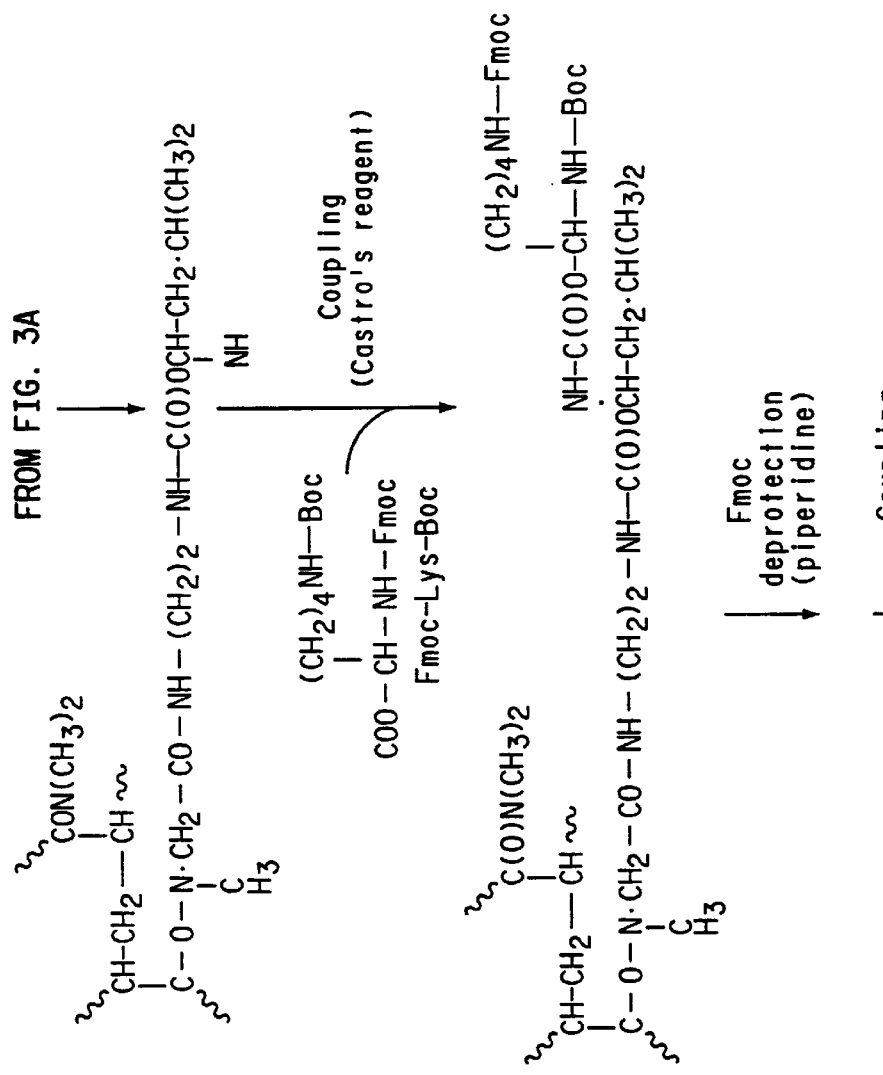
Figure 4A:
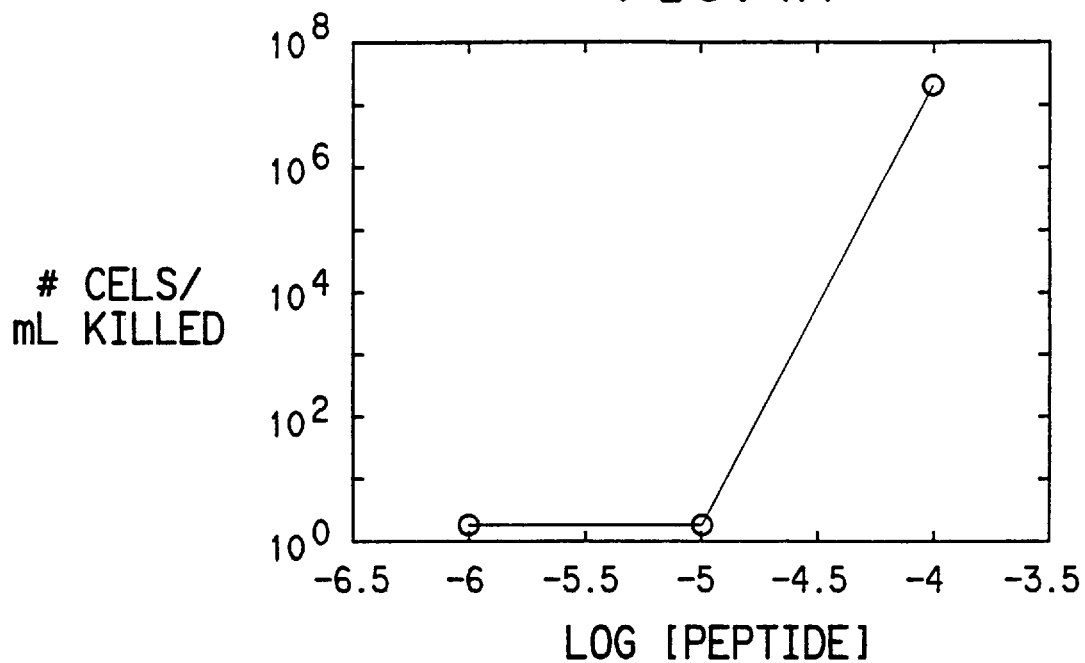
FIG. 4a illustrates cell growth inhibition of E. coli by the core oligopeptide corresponding to formula I.
Figure 4B:
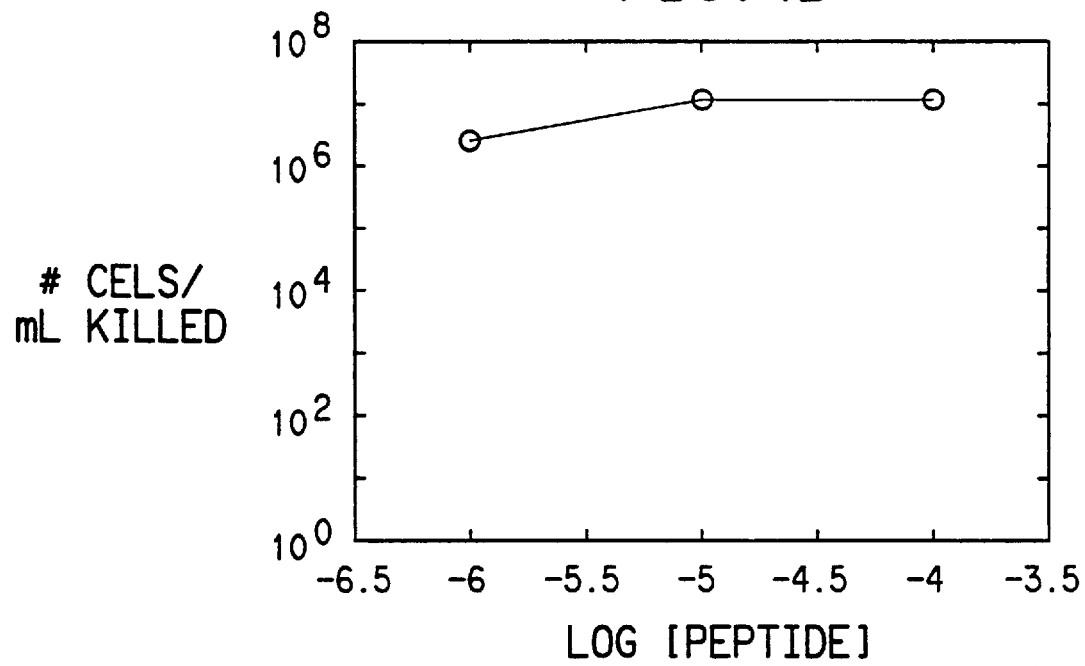
FIG. 4b illustrates cell growth inhibition of E. coli by the N-addition analogue corresponding to formula II.

It is contemplated that antimicrobial peptides attaining secondary structure similar to that of the peptides of the instant invention may be modified for the purpose of covalent attachment to a polymer. Accordingly the present invention provides a series of non-natural peptides useful as precursors for covalent incorporation into a polymer. These peptides can be incorporated into the polymer as outlined in FIG. 3. Upon subsequent deprotection of the modified peptide a peptide-bound polymer that is useful as an antimicrobial agent will result. Any of the peptides described in this invention as well as other antimicrobial peptides which share similar structural features (e.g., magainins, cecropins) may be modified at the N-terminus. The side chains of the amino acids in any of these antimicrobial sequences are appropriately protected with labile protecting or blocking groups.

It is also contemplated that the introduction of one of a number of activated functionalities (e.g., vinyl groups, bis or monoalkylamines) via a spacer group of a suitable length would be possible without significantly altering the antimicrobial activity of the subsequently formed polymer after full removal of the peptide side-chain protecting groups. Thus, the nature of the pendant modifying group is not limited in this invention. For the purpose of the present invention, but not to be limiting, suitable N-terminal modifying groups may be selected from the group comprising Lys, Lys(e-Boc), Lys(a-Boc), acyl halide, epoxy, carboxy, isocyanate, hydroxyl, alkenyl halide and acryloyl.

Peptide synthesis

The oligopeptides of the present invention may be prepared by any method known in the art, but generally will be prepared by manual or automated solid phase peptide synthesis (SPPS). An automated solid phase peptide synthesis method is preferred because it is readily adaptable to large scale commercial production.

The concept of SPPS is known in the art and has been outlined in FIG. 1. Briefly, an N-α-derivatized amino acid (AA1) is attached to an insoluble solid (R) support via a linker. The amino acid may be attached directly to the linker-support or first attached to the linker, with subsequent attachment of the amino acid-linker to the support. The N-a-blocking group (T) is then removed (deprotected) and the amino acid-linker-support is thoroughly washed with solvent. The next amino acid (AA2) (which is N-α-X-protected) is then coupled to the amino acid-linker-support as either a preactivated species (i.e., symmetrical anhydride, active ester) or directly (in situ) in the presence of activator. Coupling may also be carried out using peptides instead of single amino acids, where the peptide is N-α and side chain protected. After this reaction is complete, the N-α-dipeptide (or oligopeptide)-linker support is washed with solvent. The deprotection/coupling cycle is repeated until the desired sequence of amino acids is generated. The peptide-linker-support is cleaved to obtain the peptide as a free acid or amide, depending on the chemical nature of the linker. Ideally, the cleavage reagent also removes the amino acid side chain protecting groups, (○) which are stable to the deprotection reagent. These steps may be carried out as either a batch process, where the support is filtered between each step, or as a continuous flow process, where the support is always solvated during reagent exchange.

Currently there are a wide variety of resin supports commercially available for SPPS. A suitable support must be in particle or a physical size and shape that will permit ready manipulation and rapid filtration from liquids, and yet be inert to all reagents and solvents used during the synthesis of the peptide. For the purposed of the present invention suitable resin supports include but are not limited to cross-linked polystyrene and polyamide resins where the polystyrene resin bearing the trade mark SASRIN (BaChem Biosciences, Ltd.) is most preferred.

Although butyloxycarbonyl (Boc) is an effective blocking group it requires repetitive acidolysis for deprotection which may disrupt acid sensitive peptide bonds and give rise to catalyzed side reactions. A more acid labile N-α-amino blocking group is the base labile 9-fluorenylmethoxycarbonyl (Fmoc) group. Fmoc may be bonded to the α-amino group of an amino acid. Where the first amino acid to be attached to the resin is Fmoc protected it may be attached via an acid sensitive linker employing a coupling agent diisopropyl carbodiimide (DIC) and non-nucleophilic bases. Fmoc protected amino acids may subsequently be deprotected by base (usually piperidine). The second Fmoc amino acid is then coupled as either a preactivated species (i.e., ester or symmetrical anhydride) or without preactivation (in situ), where several different activators may be utilized. After the desired peptide sequence has been obtained, the peptide-support and the base stable side chain blocking groups are acid (usually TFA) cleaved. A review of typical solid phase peptide synthesis methods is given by J. M. Stewart, J. D. Young, in *Solid Phase Peptide Synthesis,* 2nd Edit., Pierce Chemical Co., 1984).

In a preferred embodiment peptide syntheses employs a sequential strategy using Fmoc-blocked alpha amino acids, an acid sensitive resin, (SASRIN) Boc-blocked epsilon lysine amino acids and common deprotection and coupling chemistry, known to one skilled in the art of peptide synthesis. Initially the polystyrene resin is activated with the attachment of an acid linker. Coupling of the first amino acid to the solid support is performed with diisopropylcarbodiimide, dimethylaminopyridine and N-methyl-morpholine. Attachment of the second and remaining amino acids in the sequence is achieved through removal of the Fmoc blocking group with pipiridine followed by the coupling step with Castro's reagent (benzotriazole-1-yl-oxy-tris (dimethylamino)-phosphoniumhexafluorophosphate), and diisopropyl-ethylamine. Deprotection and coupling are repeated for each subsequent amino acid to be added until the peptide synthesis is complete. The final peptide product may be deprotected with and cleaved from the resin with 25% TFA and neutralized in pyridine for incorporation into polymer compositions. Alternatively, the peptide may be cleaved from the resin in protected form with 1% TFA for use as a soluble antimicrobial.

For the purpose of permanent covalently bonding of the peptide to a polymer, an N-terminal modifying group comprising either a monoamine or bisamine derivatized blocked peptide may be constructed. Attaching the terminal modifying group to either the core or one of the N-addition analogues is achieved either (a) by the employment of the solid phase method described for the previous amino acid residues or (b) by solution reaction of the cleaved side-chain protected peptide with an appropriate compound via either the free amino or carboxy terminus.

Figure 2:
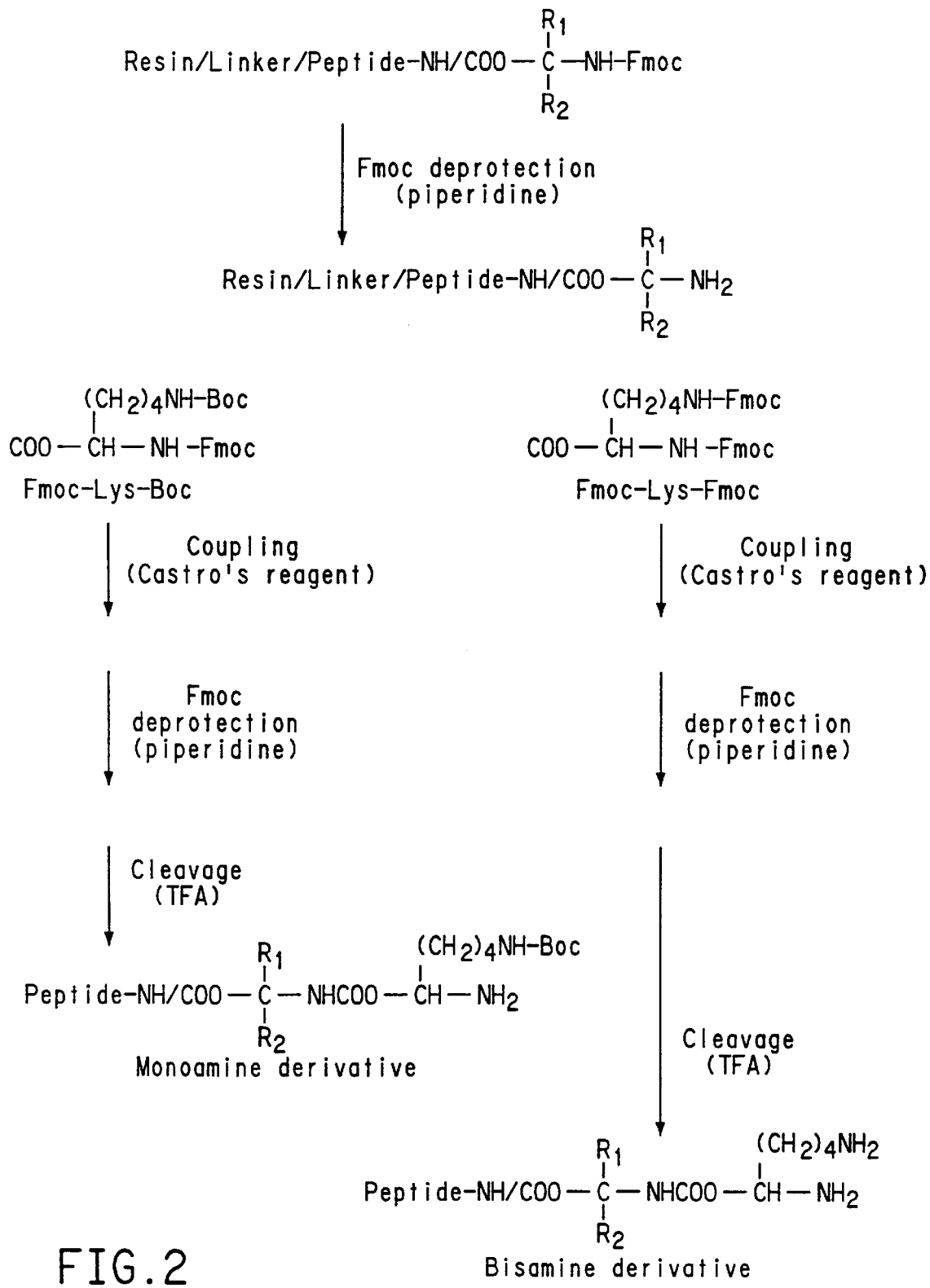

One possible scheme for the construction of monoamine and bisamine derivatized peptides is illustrated in FIG. 2. Preparation of an N-terminal Fmoc protected peptide may be prepared by solid phase peptide synthesis as described above. Before cleavage from the resin the peptide is deprotected in standard fashion with piperidine and coupled to either an Fmoc-Lys-Boc or Fmoc-Lys-Fmoc activated amino acid with standard coupling reagents used in SPPS. Following Fmoc deprotection and cleavage from the resin with TFA the Fmoc-Lys-Boc addition gives rise to the monoamine peptide derivative while the Fmoc-Lys-Fmoc addition give rise to the bisamine peptide derivative. Cleavage with 25% TFA will give the fully deprotected oligopeptide, whereas treatment with 1% TFA will give lysyl-side chain-blocked oligopeptides. It is further contemplated that a more exhaustive one-step solid phase synthetic scheme could be employed to prepare oligopeptides that are of higher purity as taught by Funakoshi, S. et al., *Proc. Natl. Acad. Sci. USA,* 88, 6981–6985, 1991). It is also contemplated that peptide monomers containing a pendant vinyl functional group for polymerizing into polymers can be prepared by SPPS employing the method described by Matsuda et al (JP 3291298)

It is contemplated that a variety of other functional peptide derivatives may be constructed where specific modifications and variations can be produced by methods well known to those skilled in the art of organic synthesis.

Although specific amino acid sequences have been defined, one of ordinary skill in the art will realize that this invention provides a basic amino acid sequence upon which many modifications and variations are possible, provided that the juxtaposition and total number of hydrophobic and basic hydrophilic amino acids falls within the limitations disclosed herein. These limitations do not preclude the possibility that the oligopeptides of the instant invention may also be produced by recombinant organisms by methods well known to those skilled in the art of genetic engineering.

Peptide-Polymer Composition

The present invention also provides a product composition comprising an effective antimicrobial peptide sequence incorporated into a polymer. The polymer may be natural or synthetic and may be selected from the group comprising polyesters, polyamides (e.g., Nylons 6, 66, 11, or 610), polyurethanes, polyolefins, polyacrylates, polysaccharides (e.g., chitin, cellulose, or algenate), polyamide coated diatomaceous earth, cellulosics, silks, nylons, biopolymers (e.g., elastin, collagen, or zein) or any polymer of synthetic or biological origin that can be formed into an object and that allows contact of the oligopeptide with the microorganism within the matrix of the polymer. For the purposes of the present invention polymers containing either silk, polyamides, polystyrenes or polyurethanes are preferred. The antimicrobial peptide sequence usually constitutes the minor component of the composition and can be present in amounts ranging from 1 to 15 percent based on weight. It is contemplated that any antimicrobial peptide sequence may be incorporated into the preferred polymers where peptides that form amphiphilic helices are preferred. Examples of such peptides may include but are not limited to, the core oligopeptide, the N-addition analogues of the core oligopeptide, as well as the naturally ocurring magainins, cecropins, protamines and their derivatives.

Preparation of Peptide-Polymer Composition

Incorporation of the bioactive peptide or oligopeptide may be accomplished either by a process of coating or spinning effective amounts of the peptide onto the desired polymer or by a reactive process resulting in the covalent bonding of the peptide to the polymer.

Active preparations of the oligopeptide and polymer involving a coating process can be prepared in a film or fiber form by one of several methods. In one embodiment, active film or fiber preparations can be made by coating the shaped object with the oligopeptide from an aqueous solution containing from about 1 to 15 weight percent of the oligopeptide. The coating solutions may also contain other small water-soluble molecules such as salts that will neither augment nor interfere with the antimicrobial action of the oligopeptide.

In another embodiment, active preparations of the antimicrobial oligopeptide and polymer can also be made by preparing a solution or mixture of the oligopeptide and the polymer, (hereinafter referred to as a "dope mixture"), and casting or forming the shaped article, fiber or film from the dope mixture. The shaped article, fiber or film containing the oligopeptide may be quenched in a suitable non-solvent. For example, dope mixtures comprising polyurethane and the core oligopeptide may be quenched in water or methanol. The shaped article, fiber or film containing the core oligopeptide may also be formed by allowing the shaped article to dry in air or under a suitable atmosphere to prevent undesirable oxidative reactions.

In another preferred embodiment the present invention also provides a method of preparing a drawn silk fiber with the oligopeptide by a process that involves: solubilizing the oligopeptide in a solvent; mixing the oligopeptide solution with a solution of natural or an unnatural silk in the same solvent; forming the fiber from a microscale spinning apparatus; and drawing the fiber to its maximum extension over a 24 hour period followed by drying. The solvent must be inert so as to cause minimal chemical changes to the composition. Solvents for the solubilization of the oligopeptide may include any inert solvent or combinations of inert solvents with power to mutually dissolve the oligopeptide and the polymer to high enough concentrations such that the final working dope solution is viscous enough to permit the drawing or fibers or making of films. For the purposes of the present invention prefered solvents include hexafluoroisopropanol or 70 weight percent lithium thiocyanate in water.

Forming the fiber composition of the oligopeptide and silk may be accomplished by any method known to one of ordinary skill in the art, however the process that is most preferred is a microscale spinning process described by Lock et al. in commonly owned U.S. Ser. No. 07/827,141 herein incorporated by reference. In the preparation of the oligopeptide-silk fiber composition it is desirable to prepare a fiber with a low denier. The lower denier fiber incorporates the advantage of achieving a "tighter" weave and better barrier against the penetration of infectious agents or fluids as well as a larger surface area for coating of effective bactericidal or antiviral agents. This larger surface area increases the likelihood that the anti-microbial agent will effectively present itself against the contaminating medium.

A silk fiber with lower denier or a smaller radial thickness is prepared with increasing quantities of the oligopeptide in the dope. Levels of oligopeptide present at 2.5 to 10 percent based on weight will effect a larger fiber draw and decrease the denier 20 to 30 percent.

In an alternative embodiment the peptides of the instant invention may be covalently incorporated into polymer compositions. As is known to those skilled in synthetic polymer chemistry, once a polymer or oligomer such as a polypeptide that has one functional group or two functional groups at one end of the polypeptide, the polypeptide can be incorporated into a synthetic (nonpolypeptide) polymer as a pendant group, also called a side chain. The synthesis of such polypeptides is described above. It is preferred that there not be any other functional groups on the polypeptide that can take part in the reaction which joins the polypeptide to the synthetic polymer, or a monomer which will be used to make a synthetic polymer. If such other functional groups are present, the polypeptide may serve to crosslink the synthetic polymer, thereby not being simply a side chain. Preferred functional groups to be placed on the end of the polypeptide are amino and hydroxy.

If one functional group is present at the end of the polypeptide, the polypeptide can be joined to the synthetic polymer in the two following ways. The polypeptide can be bonded to a molecule which can later act as a monomer which forms a synthetic polymer. For example, a polypeptide with a hydroxyl or amino end can be reacted with an isocyanate containing monomer such as 2-isocyanatoethyl methacrylate, the hydroxyl or amino groups reacting with the isocyanate group to form a urethane or a urea, respectively. The resulting methacrylate can then be free radically polymerized by itself or copolymerized with other free radically polymerizable monomers such as other (meth) acrylates or styrene, to form a copolymer. The polypeptide will be a side chain on this synthetic polymer. Alternately, the 2-isocyanatoethyl methacrylate can be (co)polymerized to form a synthetic polymer, and then the amine or hydroxy terminated polypeptide can be reacted with the isocynate groups in the polymer, so that the polypeptide again becomes a side chain on the synthetic polymer. Similar reactions on terminal mono- functional polypeptides can be carried out with other functional groups (for instance, epoxy) present in monomers for synthetic polymers, or in the synthetic polymers themselves.

Terminally difunctional polypeptides can also become side chains in synthetic polymers. For instance, these difunctional polypeptides can be used as monomers in certain condensation polymerizations, particularly when one or more of the functional groups participating in the formation of the synthetic polymer are also the functional groups on the end of the polypeptide. For example, when the two functional groups on the end of the polypeptide are amino, reaction with diacyl halides (and optionally and preferably other diamines) will yield a polyamide with pendant polypeptide groups. If the functional groups on the polypeptide are hydroxyl, reaction with diacyl halides (and preferably other diols) will lead to a polyester. Reaction of ends having 2 amine or 2 hydroxyl groups with a diisocyanate, or a so-called urethane prepolymer, will lead to a polyurea, or a poly(urethane-urea), or a polyurethane with pendant polypeptide groups. Given the relatively low thermal stability of polypeptides compared to many synthetic polymers, polymerizations that can be carried out a relatively low temperatures are preferred.

As those skilled in synthetic polymers realize, with the variety of functional groups available on the ends of these polypeptides, the above description merely gives some of the possibilities for making synthetic polymers with pendant polypeptide groups, both, from the point of view of the type of synthetic polymer made, and also the reactions used to attach the polypeptide to a synthetic polymer, or monomers used to make a synthetic polymer.

In another embodiment, bioactive peptides may be covalently attached to polymer compositions as side chain moieties by first modifying a suitable support with a non-cleavable linker followed by attachment of the carboxyl terminal amino acid to the linker, elongation of the peptide chain by repeating the steps in solid phase peptide synthesis to synthesize the full antimicrobial peptide sequence and finally removal of all side chain protecting groups. One specific instance of this embodiment is outlined in FIG. 3. Here, a polyamide resin is modified by the addition of ethylenediamine (EDA) to provide a resin with an amino functional group. Sequential additions of N-α-Fmoc and N-ε-Boc blocked amino acids may then be made using the coupling and deprotection chemistry of SPPS as outlined above.

Alternatively, when a non-specific prederivatized support is employed, then several different peptides may be reacted simultaneously to create a support with broad spectrum biocidal activity. Conversely, when the peptide-support is prepared by conventional strategy as used in solid phase peptide synthesis except that a non-hydrolyzable linkage is created between peptide and the support, only one type of antimicrobial peptide may be attached to the support. The latter approach has the advantage of providing a very specific and direct approach for determining whether the antimicrobial peptide is effective when attached pendant to a polymer and restricted to surface penetration of the microorganism.

Demonstration of Antimicrobial Activity

Determination of antimicrobial activity of the core oligopeptide, the N-addition analogues as well as the polymer compositions containing these oligopeptides may be accomplished by standard techniques. For the purposes of the present invention *Eschericia coli* or *S. aureus* are preferred.

All manipulations with microorganisms involved the application of standard sterile techniques and materials commonly employed in microbiology. All cells were grown at 37° C. and cell concentrations were measured by optical density measurements at 600 nm in a Perkin Elmer Model 552 UV/VIS spectrophotometer. For determination of antimicrobial activity of soluble oligopeptides, stationary cultures are preferred whereas culture tubes or shake flasks are preferred when the compositions are insoluble in aqueous media.

Typically, assays for antimicrobial activity of soluble oligopeptide compositions were carried out in microtiter wells. Each well was charged with 150 μl of LB broth containing cells at a final concentration of between $1 \times 10^6$ to $1 \times 10^7$ cells/ml and oligopeptide at final concentrations of $1 \times 10^{-3}$ to $1 \times 10^{-6}$M. It is preferred that the oligopeptides be dissolved in water prior to addition to the assay medium and that cells be inoculated from mid-log phase cultures. Cells were incubated at 37° C. until reaching a cell density corresponding to an absorbance reading of 0.1 A at 600 nm, at which point periodic absorbance readings were taken to determine which cultures demonstrated cell growth inhibition. Cultures showing cell growth inhibition were incubated for an additional 15 hr. at which time a final absorbance reading was taken. FIGS. 4a–d illustrate the cell growth inhibition of *E. coli* cultures incubated in the presence of various oligopeptides.

In situations where the oligopeptide compositions were insoluble in aqueous media, a culture tube or shake flask culture method is preferred. Oligopeptide compositions comprising a polymer or a fiber are examples of such insoluble oligopeptide compositions.

Insoluble oligopeptide compositions were prepared as described above. Sterile culture tubes containing about 5 ml of LB broth were inoculated with cells and oligopeptide compositions. The preferred final cell density for this assay is between $1 \times 10^6$ to $1 \times 10^7$ cells/ml where cells are inoculated from mid-log phase cultures. Weight percent of oligopeptide in the insoluble compositions were on the order of 0.018% to 15%. At periodic intervals aliquots were removed from the culture tube and transferred either to a disposable semi-microcuvette or to a microtiter plate cell for absorbance readings on a uv/vis spectrometer at 600 nm or the microplate reader at 590 nm, respectively. FIG. 5 illustrates cell growth inhibition, plotted as absorbance at 600 nm as a function of time. Although any amount of oligopeptide may be present in the insoluble oligopeptide compositions it is preferred that the oligopeptide be present at concentrations greater than or equal to 10% by weight of the total compositions.

Occasionally, a shake flask method was employed for insoluble articles. In the shake flask method, 75 mL of 0.6 mM phosphate buffer, pH 7.2 and 0.100 mL of the stock cell culture and the oligopeptide sample were added to a 250 mL polystyrene tissue culture flask. The flasks were incubated in a shaking water bath at 37° C. At specified times (1 hour and 24 hours), an aliquot (0.100 mL) was removed from the shake flask and serial dilutions ranging from 10 to 1000-fold were made to allow the enumeration of cells on agar plates. Each agar plate was inoculated with 0.200 mL of the diluted cell suspension, and the suspension was uniformly spread on the plate. Colony-forming units CFU on the agar plates were counted after 24 hours in an incubator (37° C.). Cells were identified by visual observation and use of a colony counter. Total CFU/mL was determined by correcting the cell count for the dilution factor.

The present invention provides a method of killing microorganisms with the oligopeptides and water-insoluble films, fibers or fabrics containing the antimicrobial oligopeptides. The oligopeptide or the shaped articles containing the oligopeptide is placed in contact with solutions containing microorganisms at concentrations up to $10^8$/mL with all essential growth nutrients for the microorganism. Contact times of 1 to 24 hours in media at temperatures in the range of ambient and 37° C. are effective in inhibiting growth of all gram negative bacteria, gram positive bacteria and yeasts present at concentrations equal to and less than $10^8$/mL.

As has been mentioned the peptides of the instant invention rely on their unique amphiphilic secondary structure for their antimicrobial activity. Although the entire mechanism of action for antimicrobial peptides forming amphiphilic helices is unknown, several partial explanations have been put forth in the art. Juretic et al. (FEBS, 249, 219–223, (1989)) and Westerhoff et al. (*Proc. Natl. Acad. Sci, USA,* 86, 6597–6601, (1989)) teach that the mechanism of action of magainin and its analogues is membrane depolarization to prevent respiration or oxidative metabolism. The site of oxidative metabolism is the inner membrane of the microorganism. Zasloff (WO 9004408) teaches that the peptides must be of sufficient length (>20 peptide residues) to span the lipid bilayer membrane to cause membrane perturbation. Zasloff also teaches that the activity of these peptides is potentiated in the presence of toxic anions, which supports the suggestion that ion channel formation is the mode of microbial killing. Cruciani et al., (*Biophys. J.* 53, 9a, (1988)) demonstrated that these peptides form anion-selective channels with synthetic lipid bilayers and Urritia et al., (FEBS 247, 17–21, (1989)) suggests that ion channel formation by antimicrobial peptides occurs by aggregation of the peptides. One would expect that an antimicrobial peptide which relies on its amphiphilic secondary structure for bioactivity such as magainin or the peptides of the instant invention would be precluded from forming such self-associated, multimeric channels when the peptide is covalently bound to a rigid support. Thus it is highly unexpected that such a peptide could be covalently bonded to a polymeric support and still retain its biological activity.

The following non-limiting examples are meant to illustrate and exemplify the invention but are not meant to limit it in any way.

EXAMPLES

General Methods

The growth medium may be common commercial preparations such as LB broth or containing yeast extract, Tryptone or hydrolyzed protein, sodium chloride in water. Other growth media may be used and the appropriate medium for growth of the particular microorganism will be known by someone skilled in the art of microbiology. Solutions containing none or incomplete nutrients for growth may be sterile saline, distilled water or solutions containing other salts or ingredients dissolved in saline or water and this final solution is not sufficient to support growth of microorganisms but is also non-lethal to the microorganisms.

All peptides were synthesised using the technique of solid phase peptide synthesis (SPPS) and employing methods and materials well known to those of skill in the art. All amino acids used were purchased in protected form from either BaChem Biosciences, Ltd. (Philidelphia, Pa.) or Millipore Corp. (Boston, Mass.) Protocols for SPPS are well known in the art and descriptions may be found in Stewart et al *Solid Phase Peptide Synthesis,* 2nd Edit, J. M. Stewart, J. D. Young, 1984, Pierce Chem. Co. pp 18–27 or G. A. Grant, Synthetic Peptides: *A Users Guide*, Freeman, NY, pp 77–260 herein incorporated by reference.

Example 1

Preparation of Oligopeptides

Peptide synthesis of Formulae I–IV (Table I) was accomplished using manual solid phase peptide synthesis (SPPS). The strategy employed the use of Fmoc-amino acids and a super acid-sensitive resin to prepare the peptides I–IV and their fully protected analogues. All reagents and solvents were of analytical purity or HPLC grade, respectively, and were used without further purification. Alpha-amino-Fmoc-protected amino acids (Bachem Biosciences, Philadelphia, Pa.) were used. The epsilon amino side chain of Lysine was protected with the group tert-butyloxycarbonyl (Boc). The solid phase support was SASRIN resin (2-methyoxy-4-alkoxy-benzyl alcohol derivative of a crosslinked polystyrene; Bachem Biosciences, substitution level=0.9 mequiv/gm). The first amino acid was anchored to the resin using diisopropyl carbodiimide (DIC) in the presence of dimethylaminopyridine (DMAP) and N-methyl-morpholine (NMM). Subsequent amino acids were added to the resin with the reagent that forms in situ active esters.

In a 50-mL round-bottomed flask, DIC (1.56 mL, 10 mmol) was added to a cooled solution of Fmoc-Leu-OH (3.53 g, 10 mmol) dissolved in 30 mL dichloromethane (DCM). The solution was stirred for 10' and the ice/water bath was removed and the solution was allowed to stir for another 10' before the addition of DMAP (61 mg, 0.5 mmol) and NMM (0.293 mL, 2.67 mmol). The reaction mixture was transferred to a 500-mL SPPS vessel that contained 2.3 g of SASRIN resin (2.0 mequiv). The flask was rinsed with an additional 20 mL DCM and the mixture was allowed to stir overnight. The soluble components were flushed and the resin was washed: DCM (4X); methanol, MeOH (3X); dimethylformamide (DMF, 3x); DCM (3X) and MeOH (3X). The resin clump was transferred to a preweighed coarse fritted funnel, washed with MeOH and allowed to dry to constant weight to determine yield. Yield=82%. The unreacted sites on the resin are capped by reaction with acetic anhydride. The resin is transferred back into the SPPS vessel and suspended in 20–30 mL DCM. In a separate flask, the following are mixed: acetic anhydride (0.47 mL, 5 mmol); N,N'-diisopropylethylamine (DIEA; 4.0 mL of 0.5M solution in DCM; 2.0 mmol); DCM (15 mL). This acetylating mixture is added to the resin suspension and allowed to react for 30' before washing (DCM, 3X; MeOH, 3X; DMF, 3X). Sequential coupling of the amino acids in the sequence as performed by a repeat of the following procedure. The terminal amino acid was deprotected by suspending the resin in 20–30 mL of 20 or 50% (v/v) piperidine in DMF. Deprotection reactions were run for 20' before draining the piperidine and washing the resin. Coupling was initiated by the addition of a solution containing: the next Fmoc-amino acid (at a 2.5 to 6-fold excess over the mequiv on the resin); BOP (5 to 12-fold excess over the mequiv on the resin) in sufficient solvent so that the molar concentration of Fmoc amino acid is about 0.25M. Following the addition of this solution is the addition of DIEA (5 to 12 fold excess over the mequive on the resin) and a rinse with the coupling solvent (DMAc) such that the final concentration of the activated amino acid is around 0.1M. The reaction is allowed to proceed for 2 to 2.5 hours at ambient temperature. The reaction mixture is washed (DMAc, 3X; MeOH, 3X; DMF, 3X) and deprotection and coupling are repeated for each subsequent amino acid to be added until the peptide synthesis is complete.

If the desired final peptide product is a deprotected peptide, deprotection and cleavage of the peptide from the resin may be accomplished with 25% TFA and the peptide neutralized in pyridine for incorporation into polymer compositions. Thus, after synthesis and Fmoc deprotection of the N-terminal amino acid, the completely deprotected oligopeptide was cleaved from the resin by treating the resin three times with 25% trifluoroacetic acid in methylene chloride.

The effluent was collected into a receiving flask sitting in an ice/water bath at 4° C. containing a stoichiometric quantity of pyridine for neutralization.

Solvent was removed by rotary evaporation without using heat. The fully deprotected oligopeptides were precipitated by addition of cold, anhydrous diethyl ether to the oil. The oligopeptide was collected as a crude white solid by filtration, vacuum dried, then redissolved in 10% acetic acid. This aqueous solution was stripped of solvent on a rotary evacuator.

Alternatively, if the desired final peptide product is a fully protected peptide, the peptide may be cleaved from the resin in protected form with 1% TFA for use as a soluble antimicrobial. Thus, the fully protected oligopeptides were cleaved from the resin by treating the resin three times with 1% trifluoroacetic acid in methylene chloride. The effluent was collected in the same manner as for the deprotected oligopeptides. After the solvent was removed, the protected oligopeptides were precipitated by addition of cold, distilled water to the oil. The flask containing the suspension sat on ice/water bath for several hours before collection of the solid by filtration.

For analysis, the oligopeptides were solubilized with 0.1% trifluoroacetic acid and analyzed by HPLC on an analytic reversed phase column (BioRad HiPore 318, 4.6 mm×25 cm), using a Waters Millennium 2010 HPLC system composed of two Model 510 pumps, Model 490E multiwavelength detector, Model 717 autosampler, column heater and a Millennium 2010 chromatography manager with a pump control module. The peptides were eluted by a linear gradient composed of buffer A, 0.1% trifluoroacetic acid in water, and buffer B, 0.1% trifluoroacetic acid in CH3CN/H20, 90/10. The gradient was run from 0 to 100% buffer B in 100 min with a flow rate of 1.0 mL/min at ambient temperature. The peptides were detected at 220 nm.

Preparative purification of the peptides was accomplished on a Waters Delta Prep 3000 System using a Vydac C4 reversed phase column (22 mm×25 cm) (The Nest Group; Southboro, Mass.). Buffer and gradient conditions were the same as described for the analytical separation with the exception of the flow rate which was at 10 ml/min. Amino acid compositions were determined on a Beckman 6300 amino acid analyzer following 6N acid hydrolysis of the peptides by standard methods.

Example 2

Tests of Antimicrobial Activity of Soluble Oligopeptides

All manipulations with microorganisms involved the application of standard sterile techniques employed in microbiology. All cells were grown at 37° C. Cell concentration was measured by optical density measurements at 600 nm in a Perkin Elmer Model 552 UV/VIS spectrophotometer. The microorganisms used were strains of *E. coli* and *S. aureus*. On the day prior to the assay, an overnight culture was prepared. On the following morning, the stationary phase cells were subcultured and allowed to grow to mid-log phase.

Each well was charged with LB Broth (150 mcL). The oligopeptide samples were dissolved in water and were added to achieve the appropriate final oligopeptide concentrations (ranging from $1\times10^{-3}$ to $1\times10^{-6}$M) Finally, cells suspended in LB medium were added to a final concentration of between $1\times10^6$ to $1\times10^7$ cells/mL. The microtiter plate was covered and allowed to gently rotate in an orbital shaker. When the cell growth was such that the optical density at 600 nm was in the range of 0.1 A, microtiter plate readings were taken at twenty to thirty minute intervals until the optical density exceeded 1.2 A. Cultures that demonstrated cell growth inhibition by the oligopeptides were allowed to grow overnight for final readings approximately fifteen hours later. Control samples used for all experiments were: (a) LB broth only=uninoculated control; (b) LB broth only+cells=inoculated control.

Data demonstrating cell growth inhibition of *E. coli* cultures is illustrated in FIG. 4a–d and in Table II. In FIGS. 4a–d cell growth inhibition is plotted as molar concentration of antimicrobial peptide as a function of the number of cells killed/ml. FIG. 4a–d illustrates the activity of the core oligopeptide, the N-addition analogue of formula II, the N-addition analogue of formula III, and the N-addition analogue of formula IV, respectively. All cultures were actively growing in log-phase and at a cell concentration of $2.0\times10^7$ cells/ml. As can be seen by the data the N-addition analogues have between 10 and 100 fold greater activity against *E. coli* than does the core oligopeptide.

TABLE II

| Peptide | Minimal Inhibitory Concentration $\mu$g/ml | |
|---|---|---|
| | E. coli | S. aureus |
| Formula I | 15.6 | 31.2 |
| Formula II | 7.8 | 15.6 |
| Formula III | 7.8 | 62.5 |
| Formula IV | 7.8 | 15.6 |

The data in Table II shows the bactericidal activity of the soluble peptides definded by the formula illustrated in Table I. Formula I corresponds to the core oligopeptide, whereas formulae II–IV correspond to the N-addition analogues. It is evident from the data in Table II that the soluble oligopeptides exhibited antimicrobial activity against both gram positive and gram negative bacteria and that there is a significant and unexpected increase in activity of the N-addition analogues over the core-oligopeptide.

Example 3

Preparation of Silk Fibroin/Oligopeptide Films

Solutions of 20% w/v silk fibroin in hexafluoroisopropanol (HFIP) (Aldrich Chemical Co., Milwaukee, Wis.) were prepared. These 20% solutions were diluted to a final concentration of 10% silk by adding aliquots of a core oligopeptide stock solution in HFIP. Four core oligopeptide/silk solutions were made corresponding to 0%, 0.018%, 0.18% and 15% oligopeptide in the composition.

Films were cast by dropping the solutions onto glass coverslips, then quenching in a large methanol bath. The films were washed extensively in water to remove traces of the organic solvents. The weights of the film samples were typically 3 to 5 mg, thus the amount of oligopeptide in each sample ranged from 3 mcg to 300 mcg. The films were used as is in the tests of antimicrobial activity.

Example 4

Preparation of Fibers from Oligopeptide and Silk Blends

Three different dope solutions were prepared containing 500 mg silk fibroin prepared as described by Lock in U.S. Ser. No. 07/827,141 herein incorporated by reference, 3 mL HFIP and 0, 13, or 56 mg of the core oligopeptide. The final percentage of core oligopeptide of the total solids in the dope solution was 0, 2.5 and 10 percent, respectively. The dope solutions were placed in small polyethylene bags, sealed then kneaded to remove any undissolved polymer or polypeptide particles. The bag containing the dope was centrifuged to remove any dissolved gases. The dope was then placed into a microscale spinning apparatus and fiber was formed by the process described by Lock in U.S. Ser. No. 07/827,141 herein incorporated by reference.

After fiber preparation, the fibers were drawn by hand while still wet with methanol (or the coagulation solvent) to their maximum extension. The drawing was performed during the 24 hour period immediately following the preparation and drying of the fiber. As illustrated by the data shown in Table III, the oligopeptide acts as a processing aid in the drawing of the silk fibers by permitting drawing of the fibers to a longer, total elongation. Table III shows the physical properties of denier, tensile, elongation and modulus of the fibers drawn containing 0, 2.5 and 10 percent of the core oligopeptide.

As can be seen by the data in Table III the denier for the silk/2.5% LKP and the silk/10% LKP is 24% and 41% smaller respectively than that of silk alone. Table III further shows that the other desirable parameters of silk fiber such as tensile, and modulus are not affected by the presence of the core oligopeptide.

TABLE III

Physical Properties of the LKP/Silk Fibroin Co-Spun Fibers

| Sample | Denier | Y.O.F. | Tensil | Elong. | Mod. |
|---|---|---|---|---|---|
| silk fibroin | 905 | 3.5 yds. | 2.04 | 47.8 | 41.8 |
| silk/2.5% LKP | 728 | 4.5 yds. | 2.22 | 27.8 | 47 |
| silk/10% LKP | 638 | 5.0 yds. | 2.13 | 19.7 | 46.2 |

Example 5

Tests of Antimicrobial Activity of Silk/Core Oligopeptide Films

In situations where the peptide or test system were insoluble, a culture tube or shake flask method was employed to test for antimicrobial activity. Antimicrobial activity of silk/core oligopeptide composition was tested in this manner.

Compositions of silk/core oligopeptide were prepared at varying percent core oligopeptide to silk as described in Example 3. Seven 10 ml sterile culture tubes were filled with 5.5 mL LB media each. Experimental tubes were inoculated with silk/core oligopeptide at varying percentage of oligopeptide to silk along with $E.$ $coli$ cells. Of the seven tubes, one contained LB medium only and one contained cells only. The silk/core oligopeptide compositions tested had either 0%, 0.018%, 0.18% or 15% core oligopeptide by weight. $E$ $coli$ cells inoculated into the tubes were taken from cultures actively growing at log-phase and were inoculated to a final concentration of between $1\times10^{06}$ to $1\times10^7$ cells/mL. At periodic intervals aliquots were removed from the culture tube and transferred either to a disposable semi-microcuvette or to a microtiter plate cell for absorbance readings on a uv/vis spectrometer at 600 nm. FIG. 5 illustrates cell growth inhibition, plotted as absorbance at 600 nm as a function of time.

As can be seen by the data illustrated in FIG. 5, cultures containing the silk/core oligopeptide at 15% oligopeptide demonstrated complete cell growth inhibition, whereas silk/core oligopeptide compositions containing less than 10% oligopeptide were ineffective in inhibiting the growth of $E.$ $coli$ cells.

Example 6

Preparation of Bisamine Derivatized Blocked Antimicrobial Peptides

A peptide of Formula VI having a bisamine funtionl lysine at the N-terminus was prepared using chemistry familiar to one skilled in the art of SPPS.

Formula VI:

(SEQ ID NO:10)

Lys-Gly-[Leu-LyS(Boc)Lys(Boc)-Leu-Leu-Lys(Boc)-Leu]$_2$

Synthesis was accomplished up to the final N-terminal amino acid using the pattern of coupling and deprotection described in Example 1. After addition of the N-terminal amino acid in any of the sequences in formulaes I–IV, the terminal amino acid was coupled in standard fashion with BOP-activated Fmoc-Lys(Fmoc). Following addition of this bis-Fmoc-amine-protected lysine, the SASRIN resin was treated with piperidine and washed. The Boc-protected oligopeptide was cleaved by treating the resin three times with 1% trifluoroacetic acid in methylene chloride, for 10–15 minutes. Work-up and isolation of the purified blocked oligopeptide with a terminal lysine commenses as described for the parent peptides in Example 1.

Example 7

Preparation of a Monoamine Derivatized Blocked Antimicrobial Peptide

Peptides of Formula VII or VIII having a monoamine funtional lysine at the N-terminus were prepared using chemistry familiar to one skilled in the art of SPPS.

Formula VII:

Lys-NE(Boc)-Gly-[Leu-Lys(Boc)Lys(Boc)-Leu-Leu-Lys(Boc)-Leu]2 (SEQ ID NO:11)

Formula VIII:

(SEQ ID NO:12)

Na(Boc)Lys-Gly-[Leu-Lys(Boc)Lys(Boc)-Leu-Leu-Lys(Boc)-Leu]$_2$

The preparation of the peptide of Formula VII or VIII proceeds as described for the parent formulae through the sequence of addition of the N-terminal amino acid. The terminal amino acid was coupled in standard fashion with Fmoc-Lys(Boc) or Boc(Lys)Fmoc. Treatment with piperidine, washing and resin cleavage with 1% trifluoracetic acid in methylene chloride, work-up and purification as described in Example 1 yielded a blocked oligopeptide with a terminal lysine with either a free alpha amine or a free epsilon amine.

Example 8

Preparation of Peptides Covalently Bound to Polyamide-Modified Kieselguhr Resins The methylester-activated polymer support PEPSYN K (Millipore Co., Boston Mass.) was first modified by reaction with neat ethylene diamine 24–48 hours at ambient temperature. The resin was washed in DMF (10X) and CH2C12 (10X), then vacuum dried. The resin was washed with 10% diethylamine in DMF, then reacted with BOP-activated Fmoc-Leucine (or the carboxy-terminal amino acid of the sequence) to link the first amino acid by the typical procedure outlined for solid phase peptide synthesis. The coupling of subsequent amino acid residues proceeded as described for the solid phase peptide synthesis (Example 1). After synthesis and Fmoc deprotection of the N-terminal amino acid, the resin was treated with 25% trifluoroacetic acid in methylene chloride to remove the Boc-protective group from all lysine residues in the sequence. The resin was washed with dilute (5%) pyridine in methylene chloride (3X), methylene chloride (10X), methanol (5X) and methylene chloride (10X), then vacuum dried. All control resins (i.e., resins with other chemical groups besides the antimicrobial peptide) were similarly treated with the sequence of trifluoroacetic acid deprotection and washing steps. The peptide bound resins were used without further treatment in the tests of antimicrobial activity. Composition and amino acid sequence of the covalently bound peptides could be confirmed by performing the entire solid phase peptide synthesis with a mixture of the non-acid sensitive ethylenediamine modified resin and a typical cleavable resin linker.

Example 9

Antimicrobial Activity of Peptides Covalently Bound to Polyamide Resin

Samples of peptides corresponding to the amino acid sequences SEQ ID NO:8, SEQ ID NO:13, SEQ ID NO:14, SEQ ID NO:15 and SEQ ID NO:1, were covalently linked to the polyamide resin PepSyn K as described in Example 10 and were tested for antimicrobial activity. Five compositions (PEPSYNK-LKP, PEPSYNK-LKPGK, PEPSYNK-LKPG$_2$K, PEPSYNK-LKPG$_3$K, and PEPSYNK-KGLKP) were tested over a range of 0 to 5 mg/ml of oligopeptide. Since the covalently linked oligopeptide/polymer compositions were insoluble, the protocol for testing antimicrobial activity was modified from that for the soluble peptide compositions of Example 2. Here, a shake flask method was employed.

In the shake flask method, 75 mL of 0.6 mM phosphate buffer, pH 7.2 and 0.100 mL of the stock cell culture and the oligopeptide samples, ranging from 0 to 5 mg/ml of oligopeptide were added to a 250 mL polystyrene tissue culture flask. The flasks were incubated in a shaking water bath at 37° C. At specified times (1 hour and 24 hours), an aliquot (0.100 mL) was removed from the shake flask and serial dilutions were made ranging from 10 to 1000-fold to allow the enumeration or cells on agar plates. Each agar plate was inoculated with 0.200 mL of the diluted cell suspension, and the suspension was uniformly spread on the plate. Colony-forming units CFU on the agar plates were counted after 24 hours in an incubator (37° C.). Cells were identified by visual observation and use of a colony counter. Total CFU/mL was determined by correcting the cell count for the dilution factor. In this manner the minimal inhibitory concentration (MIC) of oligopeptide for covalently linked compositions corresponding to PEPSYNK-LKP, PEPSYNK-LKPGK, PEPSYNK-LKPG$_2$K, PEPSYNK-LKPG$_3$K, and PEPSYNK-KGLKP were determined.

In order to determine that the compositions were not cytotoxic a hemolysis assay was preformed. A 5.0% stock cell solution of human erythrocytes in phosphate buffered saline (PBS) was prepared by suspending 2.0 mL packed human erythrocytes in 38 mL of phosphate buffered saline (10 mM sodium phosphate, 120 mM sodium chloride, 2.7 mM potassium chloride, pH 7.5). Samples of the four compositions recited above were added to microfuge tubes containing 0.5 mL of cell solution and 0.5 mL of PBS. Upon addition of sample, the vials were capped, gently homogenized, then allowed to gently shake in an incubator at 37° C. for 30 minutes. The samples were centrifuged to sediment the cells. The supernatants were transferred to cuvettes and the absorbances at 414 nm were read in a Perkin Elmer 552 spectrophotometer. The 0 and 100% hemolysis controls were PBS and PBS +1.0% Triton X-100, respectively.

Table IV presents data depicting the minimal inhibitory concentration (MIC) of oligopeptide within each of the four covalently linked oligopeptide/polymer compositions. As described in Example 8 all peptides were covalently attached to the resin via a non-cleavable linker, EDA. As can be seen by the data, covalent bonding of the antimicrobial peptides of Formula I–IV can be accomplished while maintaining the antimicrobial and non-cytotoxic properties of the peptides.

TABLE IV

| Covalently Linked Peptide/Polymer | MIC (µg/mL)* E. coli | % Hemolysis at >6 mg/mL)* |
|---|---|---|
| Pepsynk-LKP | 807 | 0.9 |
| PepsynK-LKPGK | 2213 | 0.7 |
| PepsynK-LKPG2K | 1208 | 1.2 |
| PepsynK-LKPG3K | 938 | 12.7 |
| PepsynK-KGLKP | 888 | >0.7 |

*resin alone and resin with EDA linker without attached peptides gave no antimicrobial or hemolytic activity Example 10

Regeneration of the Covalently Bound Antimicrobial Peptide-Polymers

Following use of the polyamide resin in an antimicrobial experiment, the supernatant was carefully decanted from the solid material. The polymer was separated from the original cell-containing media by suspension in autoclaved water (5X) and removal of the supernatant. The resin was then washed on a glass- fritted filter by the following: 0.02% aqueous sodium azide (1X); sterile, distilled water (5X); methanol (5X) and methylene chloride (5X). The resin was vacuum dried overnight before reuse in an antimicrobial experiment.

Example 11

Preparation of Immobilized Magainins and their Bactericidal Activities Against E. coli Example 11 demonstrates that known bactericidal amphiphelic peptides such as magainin may be immobilized on a polymer and retain their anti-microbial activity. The magainin 2-EDA-PepsynK resins were prepared using a Milligen EXCELL® Automated Peptide Synthesizer employing Fmoc-protected amino acids and BOP/HOBt with NMM to produce active esters in DMF solvent. Side-chain protecting groups for specific amino acids were: Ser(tBu); Lys(Boc); His(Trt); Glu(OtBu); and Asn(OPfp). The synthesis was started from Fmoc-Ser(tBu)-EDA-PepsynK resin (0.075 mmole; 0.3 g, 0.25 mmol/g= substitution level). This starting resin was prepared by coupling the carboxy-terminal amino acid to EDA-modified PepsynK as described in Example 8. The amino acid-EDA-PepsynK derivative (300 mg) was transferred to an empty EXCELL® reaction column and placed on the automated synthesizer. The remaining amino acids of the desired peptide were attached to the resin by repetitive deprotection, washing and coupling steps and these steps follow the standard cycles used by the EXCELL® peptide synthesizer. At the end of the synthesis, the final amino-terminal Fmoc group was removed prior to full deprotection. All of the protective groups were simultaneously cleaved by the washing of the final product in this cocktail: 95% trifluoroacetic acid; 5% thioanisole; 3% ethanedithiol and 2% anisole for 2 hr. Following deprotection, the peptide-resin was then washed extensively with the following sequence of washes: 5X DMF; 5X DCM; 5X MeOH; 5X DMF; 5X DCM; 5X MeOH and 5X diethyl ether. The resin was vacuum dried to remove final traces of cleavage cocktail or organic solvents to yield 490 mg of magainin 2-EDA-PepsynK. The amino acid composition was confirmed by performing a control synthesis using as starting material a mixture of 25% cleavable (Fmoc-Ser(tBu)—C(O)—O—Pepsyn KA) and 75% of the above-described non-cleavable resin. At the end of synthesis and full deprotection, the cleaved peptide product was isolated, purified and characterized by amino acid composition and sequence analyses. The sequence and compositions matched those of authentic magainin 2.

The derivatives of the 17-mer deletion peptide of magainin 2 and reverse magainin 2 peptide were prepared in the same manner as described above for magainin 2-EDA-PepsynK. The following amino acid derivatives were prepared and used as starting materials for the indicated polymer-peptide product: Fmoc-valine, magainin2 17-mer deletion peptide; Fmoc-glycine, reverse magainin 2.

The bactericidal activity for each immobilized peptide was determined as described in Example 9. The structures and the bactericidal activities of the immobilized peptides are shown in Table V. The relative activities against E. coli are consistent with what is known about the soluble peptides. The 17-mer deletion peptide has activity comparable to the full-length magainin. The reverse magainin is a much poorer bactericide than its normal sequence.

TABLE V

| Name | Peptide Structure | % Reduction E. coli |
| --- | --- | --- |
| EDA-PepsynK magainin2 | S-N-M-I-E-G-V-F-A-K-G-F-K-K-A-S-H-L-F-K-G-I-G (SEQ ID NO:16) | 100% |
| EDA-PepsynK magainin 17-mer deletion | V-F-A-K-G-F-K-K-A-S-H-L-F-K-G-I-G (SEQ ID NO:17) | 99.3% |
| EDA-PepsynK reverse magainin2 | G-I-G-K-F-L-H-S-A-K-K-F-G-K-A-F-V-G-E-I-M-N-S (SEQ ID NO:18) | 95.14% |

What is claimed is:

1. A polymer-oligopeptide consisting of:
   (i) a polymer covalently linked to
   (ii) an antimicrobial oligopeptide capable of attaining an amphiphilic helical secondary structure and selected from the group consisting of
   Lys Gly Leu Lys Lys Leu Leu Lys Leu Leu Lys Lys Leu Leu Lys Leu; (SEQ ID NO: 1),
   Leu Lys Leu Leu Lys Lys Leu Leu Lys Leu Leu Lys Lys Leu Gly Lys: (SEQ ID NO:2),
   Lys Gly Gly Leu Lys Lys Leu Leu Lys Leu Leu Lys Lys Leu Leu Lys Leu; (SEQ ID NO:3),
   Leu Lys Leu Leu Lys Lys Leu Leu Lys Leu Leu Lys Lys Leu Gly Gly Lys; (SEQ ID NO:4),
   Lys Gly Gly Gly Leu Lys Lys Leu Leu Lys Leu Leu Lys Lys Leu Leu Lys Leu; (SEQ ID NO:5), and
   Leu Lys Leu Leu Lys Lys Leu Leu Lys Leu Leu Lys Lys Leu Gly Gly Gly Lys; (SEQ ID NO:6).

2. The polymer-oligopeptide of claim 1 wherein the polymer is selected from the group consisting of polyurethane, polyetherurethane, polyester, silicone, polyamide, polyolefin, polypeptide, polysaccharide, cellulosic, and silk.

3. The polymer-oligopeptide of claim 2 wherein the polymer is a polyamide, a polystrene or a polyurethane.

4. The polymer-oligopeptide of claim 2 wherein the polymer is silk in fiber form.

5. The polymer-oligopeptide of claim 3 wherein the oligopeptide is linked to the polymer by a non-cleavable linker.

6. A process for inhibiting the growth of microorganisms comprising the steps of:
   (i) contacting an effective amount of the polymer-oligopeptide of claim 1 with a population of microorganisms; and
   (ii) leaving the polymer-oligopeptide in contact with the population of microorganisms for a time sufficient to inhibit microorganism growth.

* * * * *